(12) United States Patent
Kulach et al.

(10) Patent No.: US 8,060,337 B2
(45) Date of Patent: *Nov. 15, 2011

(54) METHOD AND APPARATUS FOR ESTIMATING A MOTION PARAMETER

(75) Inventors: Christopher J. Kulach, Calgary (CA); Ross G. Stirling, Cochrane (CA); James K. Rooney, Cochrane (CA); Paul R. MacDonald, Calgary (CA)

(73) Assignee: Garmin Switzerland GmbH (CH)

( * ) Notice: Subject to any disclaimer, the term of this patent is extended or adjusted under 35 U.S.C. 154(b) by 0 days.

This patent is subject to a terminal disclaimer.

(21) Appl. No.: 12/893,564

(22) Filed: Sep. 29, 2010

(65) Prior Publication Data

US 2011/0022349 A1    Jan. 27, 2011

Related U.S. Application Data

(63) Continuation of application No. 12/050,269, filed on Mar. 18, 2008, now Pat. No. 7,827,000, which is a continuation-in-part of application No. 11/681,032, filed on Mar. 1, 2007, now Pat. No. 7,467,060.

(60) Provisional application No. 60/778,793, filed on Mar. 3, 2006.

(51) Int. Cl.
  *G06F 15/00* (2006.01)
  *G01P 15/00* (2006.01)
(52) U.S. Cl. ............ 702/141; 702/160; 73/489; 73/490; 73/492; 73/510; 73/865.4
(58) Field of Classification Search .................. 702/141, 702/160, 161; 73/510, 865.4, 490, 492, 489
See application file for complete search history.

(56) References Cited

U.S. PATENT DOCUMENTS

| 5,525,901 | A | 6/1996 | Clymer et al. | 324/207.21 |
|---|---|---|---|---|
| 5,925,001 | A | 7/1999 | Hoyt et al. | 600/595 |
| 6,018,705 | A | 1/2000 | Gaudet et al. | 702/176 |
| 6,032,530 | A | 3/2000 | Hock | 73/379.01 |
| 6,052,654 | A | 4/2000 | Gaudet et al. | 702/160 |
| 6,305,221 | B1 | 10/2001 | Hutchings | 73/488 |

(Continued)

OTHER PUBLICATIONS

Fieschi M., et al., Jogging Support System with Portable Monitoring Device and Health Manage Software, 2004.

(Continued)

*Primary Examiner* — Sujoy K Kundu
(74) *Attorney, Agent, or Firm* — Samuel M. Korte

(57) ABSTRACT

A system for estimating motion parameters corresponding to a user. The system may generally include a receiver operable to receive a signal from an external source, an inertial sensor operable to be coupled with the user and arbitrarily oriented relative to the direction of user motion for generation of a signal corresponding to user motion, and a processing system in communication with the receiver and inertial sensor. The processing system can be operable to utilize the receiver signal to estimate a first parameter corresponding to a first motion parameter type, utilize the inertial sensor signal to estimate a second parameter corresponding to a second motion parameter type, generate a user-specific motion model to correlate the first parameter type and second parameter type using at least the first and second estimated parameters, utilize the inertial sensor signal to estimate a third parameter corresponding to the second parameter type, and utilize the motion model and the third parameter to estimate a fourth parameter corresponding to the first parameter type independent of the receiver signal.

14 Claims, 14 Drawing Sheets

U.S. PATENT DOCUMENTS

| | | | |
|---|---|---|---|
| 6,418,181 B1 | 7/2002 | Nissilä | 377/23 |
| 6,493,652 B1 | 12/2002 | Ohlenbusch et al. | 702/160 |
| 6,594,617 B2 | 7/2003 | Scherzinger | 702/160 |
| 6,790,178 B1 | 9/2004 | Mault et al. | 600/300 |
| 6,813,582 B2 | 11/2004 | Levi et al. | 702/141 |
| 6,826,477 B2 | 11/2004 | Ladetto et al. | 701/217 |
| 6,850,844 B1 | 2/2005 | Walters et al. | 701/216 |
| 6,876,947 B1 | 4/2005 | Darley et al. | 702/160 |
| 6,882,955 B1 | 4/2005 | Ohlenbusch et al. | 702/160 |
| 6,898,550 B1 | 5/2005 | Blackadar et al. | 702/182 |
| 6,941,239 B2 | 9/2005 | Unuma et al. | 702/141 |
| 7,200,517 B2 | 4/2007 | Darley et al. | 702/160 |
| 7,254,516 B2 | 8/2007 | Case, Jr. et al. | 702/182 |
| 7,467,060 B2 | 12/2008 | Kulach et al. | 702/141 |
| 7,774,156 B2 | 8/2010 | Niva et al. | 702/142 |
| 7,827,000 B2 | 11/2010 | Stirling et al. | 702/141 |
| 2006/0284979 A1* | 12/2006 | Clarkson | 348/143 |
| 2007/0250261 A1 | 10/2007 | Soehren | 701/207 |
| 2008/0190202 A1 | 8/2008 | Kulach et al. | 73/514.01 |
| 2011/0022349 A1 | 1/2011 | Stirling et al. | 702/141 |

OTHER PUBLICATIONS

Micorsport—Your Personal Computer, published prior to Mar. 18, 2008.

Suunto Discussions from http://www.suuntosports.com/discussions/forum_posts.asp?TID=57&FID=2, posting by wmi on Nov. 9, 2006.

U.S. Appl. No. 12/021,116, filed Jan. 28, 2008.

Notification of Transmittal of the International Search Report and the Written Opinion of the International Searching Authority or the Declaration, dated Apr. 27, 2009 from PCT/CA2009/000029, filed Jan. 15, 2009.

Fieschi M., et al., Jogging Support System with Portable Monitoring Device and Health Manage Software, 2004.

International Search Report from corresponding International Application No. PCT/CA2009/000029, dated Aug. 12, 2010.

Microsport—Your Personal Computer, published prior to Mar. 18, 2008.

Notification of Transmittal of the International Search Report and the Written Opinion of the International Searching Authority or the Declaration, dated Apr. 27, 2009 from PCT/CA2009/000029, filed Jan. 15, 2009.

Siewiorek, Daniel, et al., SenSay: A Context-Aware Mobile Phone, published prior to Jan. 28, 2008.

Suunto Discussions from http://www.suuntosports.com/discussions/forum posts.asp?TID=57&FID=2 posting by wmi on Nov. 9, 2006.

* cited by examiner

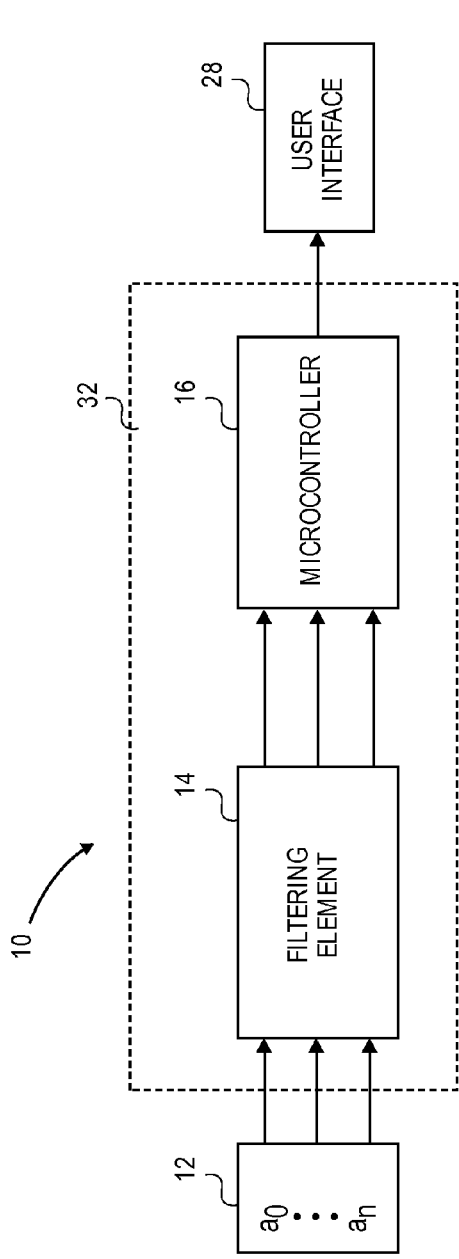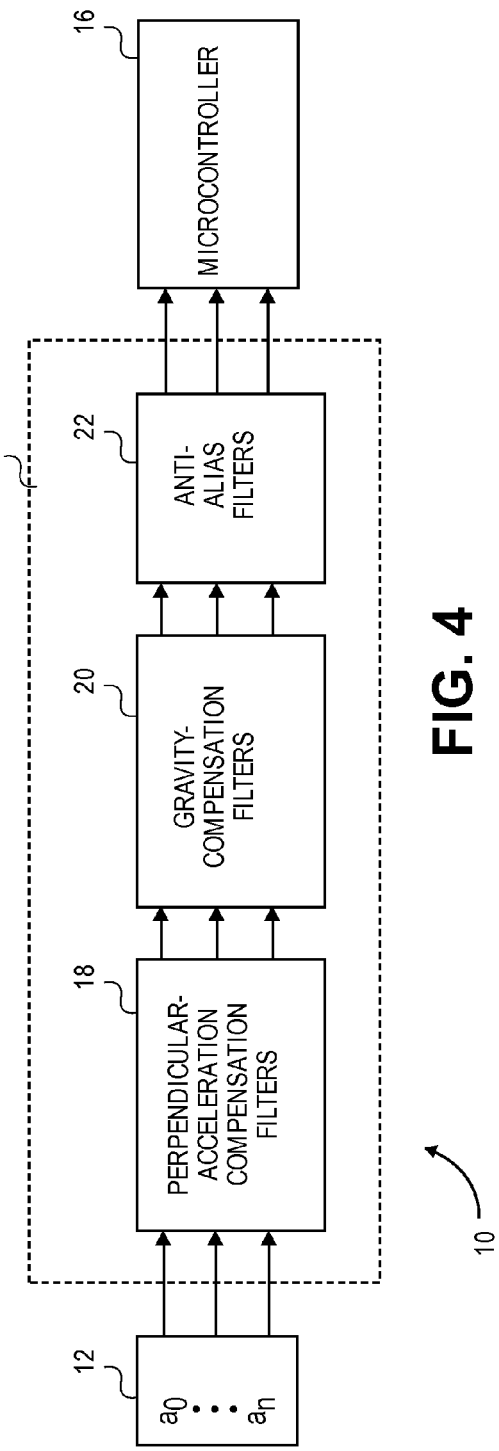
FIG. 3
FIG. 4

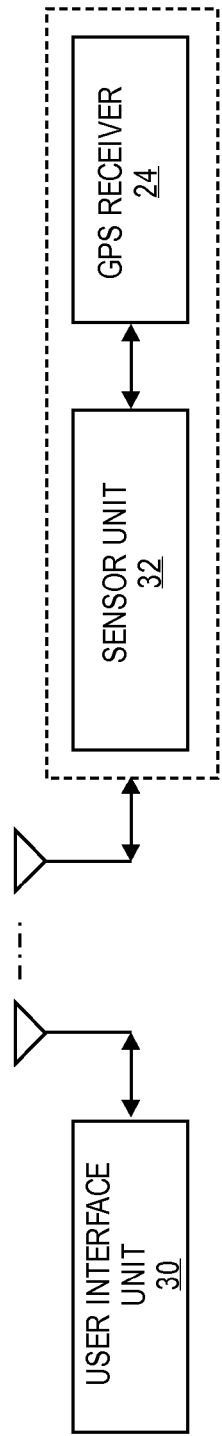
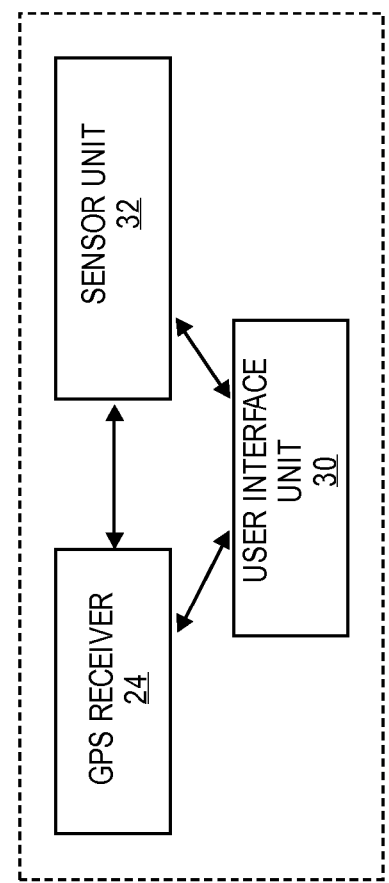
FIG. 8
FIG. 9

METHOD AND APPARATUS FOR ESTIMATING A MOTION PARAMETER

RELATED APPLICATIONS

The present application is a continuation of U.S. patent application Ser. No. 12/050,269, entitled "METHOD AND APPARATUS FOR ESTIMATING A MOTION PARAMETER," filed Mar. 18, 2008, which itself is a continuation-in-part of U.S. patent application Ser. No. 11/681,032, entitled "METHOD AND APPARATUS FOR ESTIMATING A MOTION PARAMETER," filed Mar. 1, 2007, which in turn claims the benefit of U.S. Provisional Application No. 60/778,793, entitled "METHOD AND SYSTEM FOR QUICK DISTANCE MEASUREMENT," filed Mar. 3, 2006. Each of the above-identified applications is incorporated herein by reference.

BACKGROUND

1. Field

Embodiments of the present invention relate to methods and apparatuses for estimating motion parameters. More particularly, various embodiments of the invention provide methods and apparatuses operable to generate a motion model to correlate parameters estimated using different signal sources.

2. Description of the Related Art

Motion sensing apparatuses are often used to sense the motion of an object, animal, or person. For example, estimated motion parameters, such as acceleration, average velocity, stride distance, total distance, gait efficiency, speed, cadence, and the like, may be utilized in the training and evaluation of athletes and animals, the rehabilitation of the injured and disabled, and in various recreational activities.

Some motion sensing apparatuses employ Global Positioning System (GPS) receivers and inertial sensors such as accelerometers to generate signals for motion parameter estimation. These apparatuses may often accurately estimate motion parameters, but they require the GPS receivers and inertial sensors to always be used in tandem—thereby increasing the size and power footprint of the apparatuses.

SUMMARY

In various embodiments the present invention provides a system for estimating motion parameters corresponding to a user. The system generally includes a receiver operable to receive a signal from an external source, an inertial sensor operable to be coupled with the user and arbitrarily oriented relative to the direction of user motion for generation of a signal corresponding to user motion, and a processing system in communication with the receiver and inertial sensor. The processing system can be operable to utilize the receiver signal to estimate a first parameter corresponding to a first motion parameter type, utilize the inertial sensor signal to estimate a second parameter corresponding to a second motion parameter type, generate a user-specific motion model to correlate the first parameter type and second parameter type using at least the first and second estimated parameters, utilize the inertial sensor signal to estimate a third parameter corresponding to the second parameter type, and utilize the motion model and the third parameter to estimate a fourth parameter corresponding to the first parameter type independent of the receiver signal. Such a configuration allows the estimation of motion parameters corresponding to the first parameter type (e.g., user speed) if the receiver (e.g., a navigation device). is disabled or otherwise unable to receive signals from the external source (e.g., global navigation satellites).

It is to be understood that both the foregoing general description and the following detailed description are exemplary and explanatory only and are not necessarily restrictive of the invention claimed. The accompanying drawings, which are incorporated in and constitute a part of the specification, illustrate embodiments of the invention and together with the general description, serve to explain the principles of the invention.

BRIEF DESCRIPTION OF THE DRAWING FIGURES

Various embodiments of the present invention are described in detail below with reference to the attached drawing figures, wherein:

FIG. 3 is a block diagram illustrating some of the components operable to be utilized by various embodiments of the present invention;

FIG. 4 is a block diagram illustrating some of the components of FIG. 3 in more detail;

FIG. 8 is a block diagram illustrating another configuration of the sensor unit and GPS receiver of FIG. 5;

FIG. 9 is a block diagram illustrating another configuration of the GPS receiver, user interface unit, and sensor unit of FIG. 5;

Figure 1:
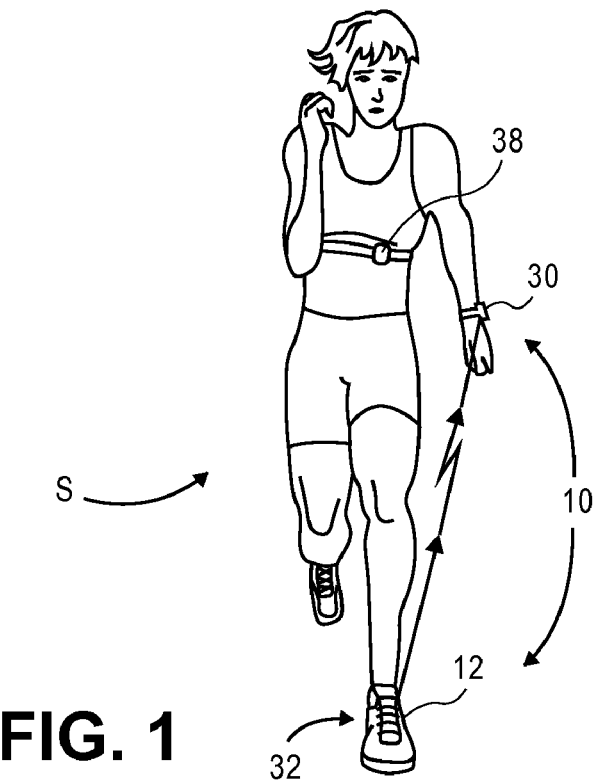
FIG. 1 is a schematic diagram illustrating a user employing a sensor unit and a user interface unit configured in accordance with various embodiments of the present invention.

The drawing figures do not limit the present invention to the specific embodiments disclosed and described herein. The drawings are not necessarily to scale, emphasis instead being placed upon clearly illustrating various embodiments of the invention.

DETAILED DESCRIPTION

The following detailed description of various embodiments of the invention references the accompanying drawings which illustrate specific embodiments in which the invention can be practiced. The embodiments are intended to describe aspects of the invention in sufficient detail to enable those skilled in the art to practice the invention. Other embodiments can be utilized and changes can be made without departing from the scope of the present invention. The following detailed description is, therefore, not to be taken in a limiting sense. The scope of the present invention is defined only by the appended claims, along with the full scope of equivalents to which such claims are entitled.

Various embodiments of the present invention provide a motion sensing apparatus 10 operable to generate a motion model using parameters estimated from a plurality of sources, such as inertial sensors and navigation devices. The motion model may be used to estimate a parameter corresponding to one of the sources if the source is unavailable. Such a configuration allows the estimation of motion parameters corresponding to a parameter type (e.g., user speed) if the apparatus 10 is unable to receive signals from an external source.

In various embodiments, the apparatus 10 can include one or more accelerometers 12, a filtering element 14, and a processing system 16. The accelerometers 12, filtering element 14, and processing system 16 may be integrated together or form discrete elements that may be associated with each other. The processing system 16 is generally operable to analyze measurements provided by the one or more accelerometers 12 to estimate parameters corresponding to one or more parameter types.

The one or more accelerometers 12 are each operable to measure an acceleration and generate an acceleration measurement corresponding to the measured acceleration. The acceleration measurement may be embodied as a signal operable to be utilized by the filtering element 14 and/or processing system 16. In some embodiments, one or more of the accelerometers 12 may be operable to output an analog signal corresponding to an acceleration measurement. For instance, each accelerometer 12 may output an analog voltage signal that is proportional to measured accelerations. In some embodiments, one or more of the accelerometers 12 may include the ADXL321 accelerometer manufactured by ANALOG DEVICES of Norwood, Mass. However, the one or more accelerometers 12 may include any digital and analog components operable to generate a signal corresponding to a measured acceleration. Thus, in some embodiments, one or more of the accelerometers 12 are operable to output a digital signal representing measured accelerations. Further, in some embodiments, one or more of the accelerometers 12 may comprise linear accelerometers.

Figure 2:
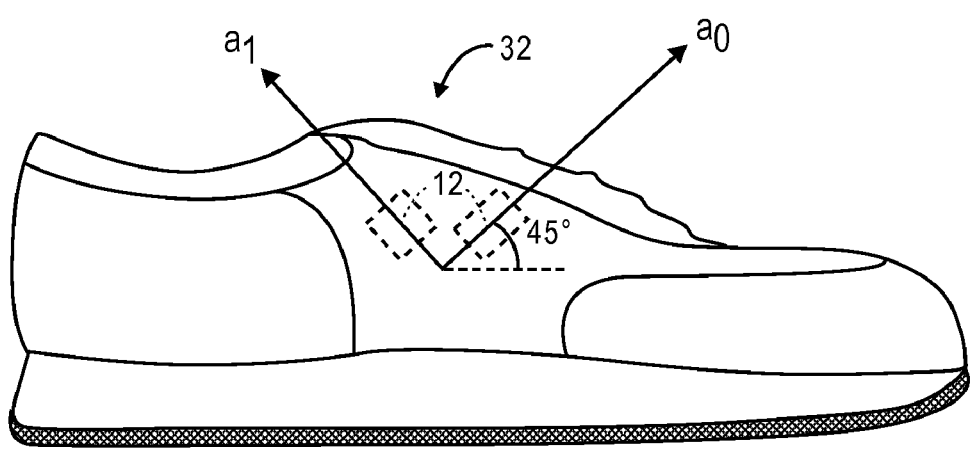
FIG. 2 is a schematic diagram illustrating an exemplary orientation of various sensors within or on a shoe.

In some embodiments, more than one of the accelerometers 12 may be integrated into the same integrated circuit package to allow the single package to provide acceleration measurements along more than one axis. For example, as shown in FIG. 2, the apparatus 10 may include two or more accelerometers 12 each operable to output a signal corresponding to a measured acceleration. In some embodiments, the apparatus 10 includes at least two accelerometers 12 adapted to measure accelerations in two directions separated by an angle greater than zero degrees and each provide a signal corresponding to the measured acceleration. Further, the apparatus 10 may include at least three accelerometers 12 adapted to measure accelerations in three directions each separated by an angle greater than zero degrees and each provide a signal corresponding to the measured acceleration. In some embodiments, the three accelerometers 12 may be oriented in a mutually perpendicular configuration. However, the apparatus 10 may include any number of accelerometers 12, including a single accelerometer 12, positioned in any configuration to provide acceleration measurements for use by the filtering element 14 and/or processing system 16.

The one or more of the accelerometers 12 may be operable to communicate with other elements of the apparatus 10, or elements external to the apparatus 10, through wired or wireless connections. Thus, the accelerometers 12 may be coupled with the filtering element 14 and/or processing system 16 through wires or the like. One or more of the accelerometers 12 may also be configured to wirelessly transmit data to other apparatus 10 elements and devices external to the apparatus 10. For instance, one or more of the accelerometers 12 may be configured for wireless communication using various RF protocols such as Bluetooth, Zigbee, ANT®, and/or any other wireless protocols.

The filtering element 14 is operable to couple with the one or more accelerometers 12 and filter acceleration measurements and/or signals corresponding to acceleration measurements. In some embodiments, the apparatus 10 does not include the filtering element 14 and the processing system 16 is operable to use unfiltered acceleration measurements and corresponding signals. In other embodiments, the filtering element 14 may be integral with one or more of the accelerometers 12, the processing system 16, or both the accelerometers 12 and the processing system 16. For example, a first portion of the filtering element 14 may be integral with one or more of the accelerometers 12 and a second portion of the filtering element 14 may be integral with the processing system 16. In other embodiments, the filtering element 14 may be discrete from both the accelerometers 12 and the processing system 16.

The filtering element 14 may include analog and digital components operable to filter and/or provide other pre-processing functionality to facilitate the estimation of motion parameters by the processing system 16. In various embodiments as shown in FIG. 4, the filtering element 14 is operable to filter signals provided by the one or more accelerometers 12, or signals derived therefrom, to attenuate perpendicular acceleration, to compensate for gravity, and/or to minimize aliasing. The filtering element 14 may include discrete components for performing each of these filtering functions or use the same components and hardware for these, and other, filtering functions.

The filtering element 14 may include any analog and digital components for filtering signals and measurements, including passive and active electronic components, processors, controllers, programmable logic devices, digital signal processing elements, combinations thereof, and the like. In some embodiments, the filtering element 14 may include a digital microcontroller, such as the MSP430F149 microcontroller manufactured by TEXAS INSTRUMENTS to provide various static and/or adaptive filters. The filtering element 14 may also include an analog-to-digital converter to convert analog signals provided by the one or more accelerometers 12 to digitize signals for use by the processing system 16. The filtering element 14 may also include conventional pre-sampling filters.

In some embodiments, the low-pass filter 18 may be an adaptive filter operable to employ static and/or varying cutoff frequencies between about 0.5 Hz and 10 Hz. In some embodiments where parameters corresponding to human strides are estimated, the low-pass filter 18 may employ cut-off frequencies between about 1 Hz and 3 Hz. The filtering element 14 may acquire the cut-off frequency from the processing system 16 based on computations performed by the processing system 16 corresponding to the particular stride frequency of the subject element S. The low-pass filter 18 may additionally or alternatively be adapted to employ a cut-off frequency corresponding to a gait type identified by the processing system 16.

In other embodiments, the cut-off frequency for the low-pass filter 18 may be a static value based upon the typical stride frequency of a running or walking human. For instance, the cut-off frequency may correspond to a frequency between one and two times the typical stride frequency of a running and/or walking human, such as a static frequency between 1 Hz and 3 Hz. Specifically, in some embodiments, the cut-off frequency may be about 1.45 Hz for walking humans and about 2.1 Hz for jogging humans.

The gravity compensation provided by the filtering element 14 generally compensates for the constant acceleration provided by gravity that may be sensed by one or more of the accelerometers 12. In some embodiments, the filtering element 14 includes a high-pass filter 20 operable to filter or attenuate components of signals corresponding to measured accelerations below a given cut-off frequency. The cut-off frequency of the high-pass filter 20 may correspond to a frequency approaching 0 Hz, such as 0.1 Hz, to adequately provide compensation for gravity-related acceleration.

The anti-aliasing provided by the filtering element 14 generally reduces or prevents aliasing caused by sampling of the signals provided by, or derived from, the one or more accelerometers 12. In some embodiments, the filtering element 14 includes a relatively wideband filter 22 designed to attenuate signal frequencies in excess of one-half of the sampling frequency used in any subsequent analog-to-digital conversions provided by the processing system 16 or other devices associated with the apparatus 10. In some embodiments, the filtering element 14 may provide other filtering components instead of, or in addition to, the wideband filter 22 to compensate for aliasing. For instance, the filtering element 14 may include one or more analog and/or digital filters to perform any combination of the various filtering functionality discussed herein. In some embodiments, a single filtering element may be utilized to perform each of the filtering functions discussed above such that separate or discrete filters are not necessarily employed for different filtering functions.

The processing system 16 is generally operable to couple with the one or more accelerometers 12 and/or the filtering element 14 to estimate a motion parameter corresponding to a motion parameter type. The processing system 16 may include various analog and digital components operable to perform the various functions discussed herein. In some embodiments, the processing system 16 may include a microprocessor, a microcontroller, a programmable logic device, digital and analog logic devices, computing elements such as personal computers, servers, portable computing devices, combinations thereof, and the like.

The processing system 16, filtering element 14, accelerometers 12, and/or other portions of the apparatus 10 may limit or expand the dynamic range of acceleration measurements used to generate the motion parameter metric and/or identify attachment position. For example, acceleration measurements outside a specified dynamic range, such as plus or minus 8 g, may be saturated at the dynamic range limits to further limit the effects of perpendicular acceleration. Alternatively, linear or non-linear amplifiers may be used to increase or reduce the dynamic range. The dynamic range may be varied by the processing system 16 based on the particular motion parameter being estimated or according to other sensed or generated measurements.

The processing system 16 may also include, or be operable to couple with, a memory. The memory may include any computer-readable memory or combination of computer-readable memories operable to store data for use by the processing system 16. For instance, the memory may be operable to store acceleration data, motion parameter metric data, statistical data, motion parameter data, filtering data, configuration data, combinations thereof, and the like.

The processing system 16 may be discrete from the various accelerometers 12 and filtering element 14 discussed above. In other embodiments, the processing system 16 may be integral with other portions of the apparatus 10. For instance, the same microcontroller or microprocessor may be utilized to implement the filtering element 14 and the processing system 16.

In some embodiments, data and information generated by the accelerometers 12, filtering element 14, and/or processing system 16 may be stored in the memory associated with the processing system 16, or in any other computer-readable memory, to allow later analysis by the processing system 16 or other devices associated therewith. The stored information may be time-correlated to facilitate analysis and compressed to reduce the required capacity of the memory.

The processing system 16 may additionally or alternatively utilize information acquired from sensors other than the one or more accelerometers 12. For instance, in some embodiments the processing system 16 may couple with a heart rate monitor 38, acquire heart rate information from the heart rate monitor 38, and generate a motion parameter using the heart rate information and/or acceleration measurements. Similarly, the processing system 16 may couple with other sensors to acquire non-acceleration kinematic variables such as velocity and/or environmental variables such as ambient temperature and altitude. For example, to acquire additional information, the processing system 16 may couple with, and/or include, radio-frequency transceivers, thermometers, altimeters, compasses, inclinometers, pressure sensors, blood pressure monitors, light sensors, atmospheric sensors, angular velocity sensors and other inertial sensors, microphones, computing devices such as personal computers, cellular phones, and personal digital assistances, other similarly configured apparatuses, combinations thereof, and the like.

In some embodiments, as shown in FIGS. 6 through 9, the apparatus 10 may be operable to receive information from at least one navigation device 24. The navigation device 24 may be adapted to provide geographic location information to the apparatus 10 and users of the apparatus 10. The navigation device 24 may include a GPS receiver much like those disclosed in U.S. Pat. No. 6,434,485, which is incorporated herein by specific reference. However, the navigation device 24 may use cellular or other positioning signals instead of, or in addition to, the GPS to facilitate determination of geographic locations. The navigation device 24 may be operable to generate navigation information such as the speed of the navigation device 24, the current and previous locations of the navigation device 24, the bearing and heading of the navigation device 24, the altitude of the navigation device 24, combinations thereof, and the like.

The processing system 16 may use the information received from the navigation device 24 to estimate a motion parameter and/or generate a motion model. The processing system 16 may also use and present acquired navigation information independent of the metrics and estimated parameters. Additionally or alternatively, the processing system 16 may use the information acquired from the navigation device 24 to correct and/or adjust calculated information. For instance, the processing system 16 may compare distances and speeds generated from accelerations provided by the one or more accelerometers 12 with distances and speeds provided by the navigation device 24 and correct calculated measurements to enable distances and speeds generated from measured accelerations to be as accurate as those provided by the navigation device 24. Thus, the processing system 16 may be periodically coupled with the navigation device 24 to correct information to ensure that the apparatus 10 accurately estimates motion parameters even when not coupled with the navigation device 24. Such functionality is discussed in more detail below.

The filtering element 14 and processing system 16 may additionally be operable to compensate for part-to-part manufacturing variability present in the one or more accelerometers 12, including characterization over temperature of zero-g bias point, sensitivity, cross-axis sensitivity, nonlinearity, output impedance, combinations thereof, and the like.

In some embodiments, compensation parameters are periodically adjusted during device use. For example, if the processing system 16 detects that the apparatus 10 is substantially stationary, the sum of accelerations provided by the one or more accelerometers 12 may be compared to an expected acceleration sum of 1 g (g is the gravitational constant, 9.81 m/s$^2$), and the difference may be used by the processing system 16 to adjust any one of or a combination of compensation parameters.

Thus, for example, if $x_m$, $y_m$, $z_m$ are acceleration measurements produced by three accelerometers 12 oriented in substantially mutually perpendicular directions and the accelerometers are at rest, the combined measured acceleration can be expected to be $x_m^2+y_m^2+z_m^2=g^2$. If it is assumed that $x_m$ and $y_m$ are accurate, then in $x_m^2+y_m^2+z_c^2=g^2$ the only unknown is $z_c$, and the processing system 16 can compute $z_c$ from $x_m$ and $y_m$ whenever the unit is mostly stationary, and compare this value to measured $z_m$. The difference between the measured acceleration $z_m$ and the computed acceleration $z_c$ can be assumed to be attributable to inadequate compensation of the z measurement for part-to-part manufacturing variability, temperature sensitivity, humidity sensitivity, etc. Consequently, an adjustment to one or more of the compensation parameters can be made based on the difference. By periodically adjusting compensation parameters based on stationary gravitational assumptions, it may thus be possible to eliminate or reduce the complexity of compensation parameter modeling in some embodiments. However, embodiments of the present invention may employ or not employ any combination of compensation methods and parameters.

Figure 5:
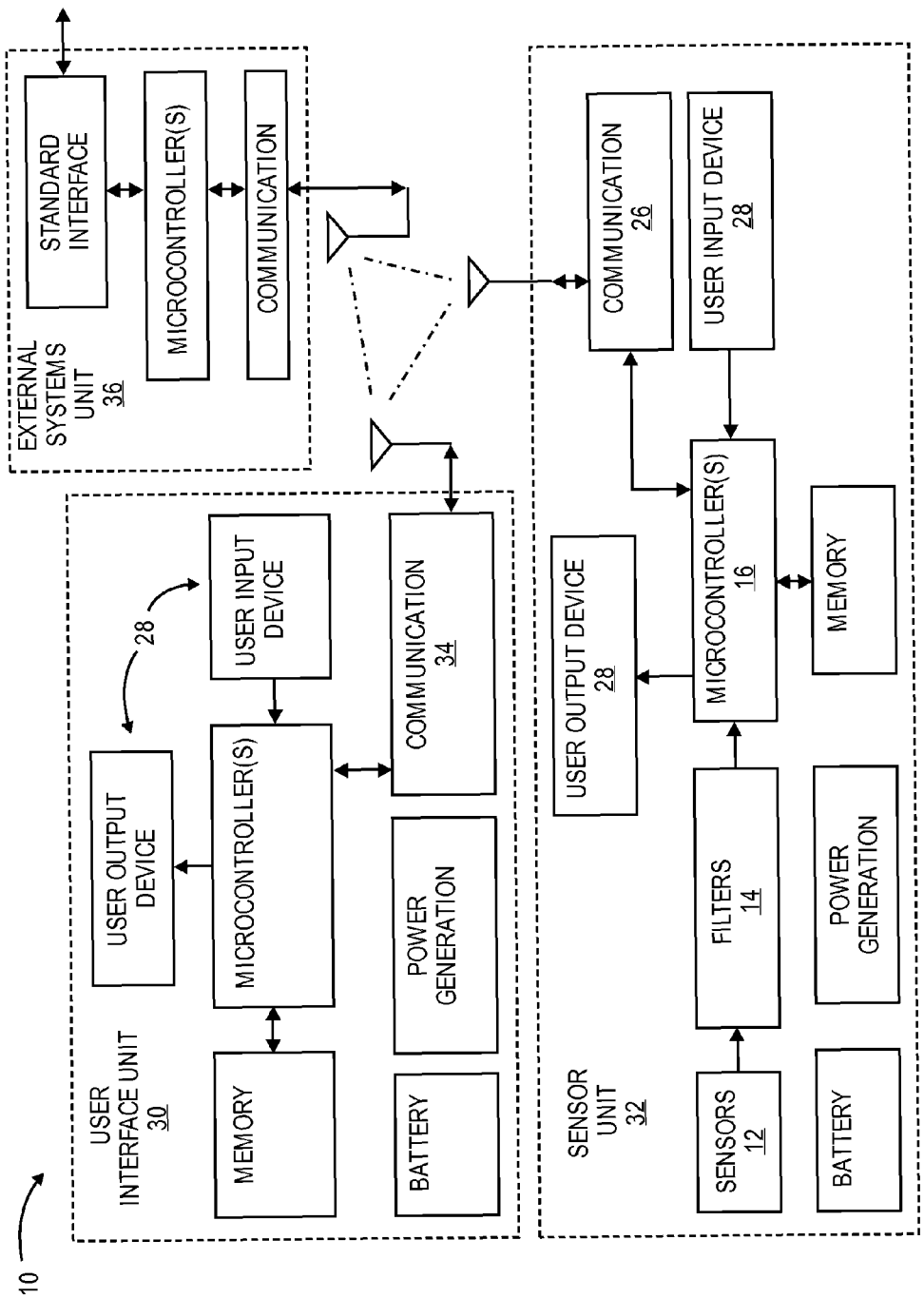
FIG. 5 is a block diagram illustrating an external systems unit in communication with the sensor unit and user interface unit of FIG. 1.

In some embodiments, as shown in FIG. 5, the apparatus 10 may include a communications element 26 to enable the apparatus 10 to communicate with other computing devices, exercise devices, navigation devices, sensors, and any other enabled devices through a communication network, such as the Internet, a local area network, a wide area network, an ad hoc or peer to peer network, combinations thereof, and the like. Similarly, the communications element 26 may be configured to allow direct communication between similarly configured apparatuses using USB, ANT®, Bluetooth, Zigbee, Firewire, and other connections, such that the apparatus 10 need not necessarily utilize a communications network to acquire and exchange information.

In various embodiments the communications element 26 may enable the apparatus 10 to wirelessly communicate with communications networks utilizing wireless data transfer methods such as WiFi (802.11), Wi-Max, Bluetooth, ultra-wideband, infrared, cellular telephony (GSM, CDMA, etc.), radio frequency, and the like. However, the communications element 26 may couple with the communications network utilizing wired connections, such as an Ethernet cable, and is not limited to wireless methods.

The communications element 26 may be configured to enable the apparatus 10 to exchange data with external computing devices to facilitate the generation and/or analysis of information. For example, the processing system 16 may use information acquired through the communications element 26 in estimating motion parameters and/or in generating motion models. The processing system 16 may also provide generated motion parameter metrics, motion models, and estimated motion parameters through the communications element 26 for use by external devices. For instance, the external devices can be configured to store, analyze, and exchange information between a plurality of users and/or a plurality of devices attached to one or multiple users.

Consequently, the communications element 26 generally enables real-time comparison of information generated by the apparatus 10 and other devices. The communications element 26 also enables the apparatus 10 to store data on one or more of the external devices for later retrieval, analysis, aggregation, and the like. The data can be used by individuals, their trainers or others to capture history, evaluate performance, modify training programs, compare against other individuals, and the like. The data can also be used in aggregated form.

The apparatus 10 may additionally include a user interface 28 to enable users to access various information generated and acquired by the apparatus 10, such as attachment positions, acceleration measurements, motion parameter metrics, estimated motion parameters, generated motion models, navigation information acquired from the navigation device 24, information and data acquired through the communications element 26, configuration information, combinations thereof, and the like. The user interface 28 facilities, for example, powering on/off the apparatus 10, selecting which content to display, and providing configuration information such as the attributes of the subject element S.

The user interface 28 may include one or more displays to visually present information for consumption by users and one or more speakers to audibly present information to users. The user interface 28 may also include mechanical elements, such as buzzers and vibrators, to notify users of events through mechanical agitation. In some embodiments, as shown in FIG. 1, the user interface 28 may be implemented within a watch operable to be worn on a user's wrist, forearm, and/or arm. Thus, the user interface 28 may be positioned separately from one or more of the accelerometers 12 to enable the user to easily interact with the apparatus 10. However, in some embodiments the user interface 28 and accelerometers 12 may be integral.

The user interface 28 may also be operable to receive inputs from the user to control the functionality of the processing system 16 and/or devices and elements associated therewith. The user interface 28 may include various functionable inputs such as switches and buttons, a touch-screen display, optical sensors, magnetic sensors, thermal sensors, inertial sensors, a microphone and voice-recognition capabilities, combinations thereof, and the like. The user interface 28 may also include various processing and memory devices to facilitate its functionality.

The user interface 28 enables users to receive real-time feedback concerning the estimated motion parameter and associated information. For instance, the user interface 28 may present the currently estimated motion parameter, such as a current stride speed and distance, and/or information associated therewith or with other motion parameters, such as total distance, calories expended, total speed, combinations thereof, and the like.

Figure 10:
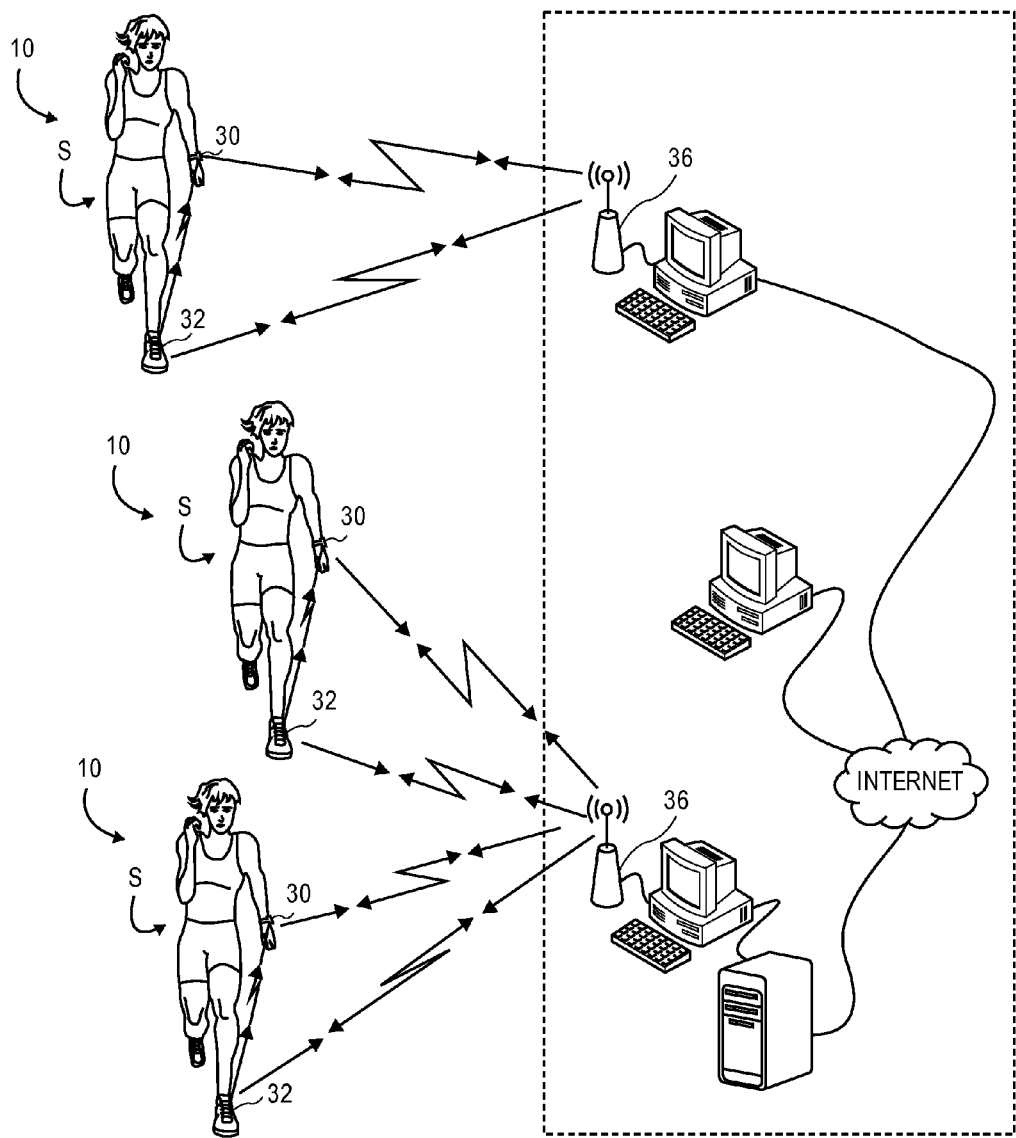
FIG. 10 is a schematic diagram showing the interaction of a plurality of apparatuses configured in accordance with various embodiments of the present invention.

Utilizing the communications element 26, the user interface 28 also enables users to receive real-time feedback and comparisons with other users and devices. For instance, as shown in FIG. 10, a plurality of apparatuses 10 may be employed by a plurality of runners to enable data, metrics, and parameters corresponding to each runner to be shared and presented to the user. Thus, for instance, the user may ascertain the speed and location of other users through the user interface 28.

Further, the user interface 28 may acquire comparison information from the processing system 16 and/or from other devices through the communications element 26 to enable the user to compare his or her performance using the comparison information. For instance, the user interface 28 may present a comparison of the user's current performance with a previous performance by the user, with a training model, and/or with another individual.

In various embodiments, the user may configure the apparatus 10 utilizing the user interface 28 to monitor estimated motion parameters and alert the user through the user interface 28 when one or more estimated motion parameters conflict with a user-defined condition such as an acceptable parameter range, threshold, and/or variance. The user may also configure the apparatus 10 utilizing the user interface 28 to monitor various user-defined goals, such as time limits, motion parameter maximum values, and the like.

As is discussed above, the various components of the apparatus 10 may be housed integrally or separately in any combination. In some embodiments, the apparatus 10 includes an interface unit 30 for housing the user interface 28 and associated components and a sensor unit 32 for housing the one or more accelerometers 12 and the communications element 26. In such embodiments, the processing system 16 (housed within both or either unit 30, 32) is operable to determine the attachment position of the sensor unit 32. In some embodiments, the units 30, 32 may be housed within the same housing, as is shown in FIG. 9. However, in other embodiments the units 30, 32 may be discrete such that the sensor unit 32 may be positioned in a first location, such as on the user's shoe, and the interface unit 30 may be positioned at a second location, such as on the user's wrist.

The interface unit 30 may also include an interface communication element 34, configured in a similar manner to the communications element 26 discussed above, to enable the interface unit 30 to exchange information with the sensor unit 32, other parts of the apparatus 10, and/or with devices external to the apparatus 10. In embodiments where the units 30, 32 are positioned separate from each other, the communications elements 26, 34 may communicate utilizing the various wireless methods discussed above. However, the communications elements 26, 34 may also communicate utilizing wired connections or through external devices and systems.

The units 30, 32 may also each include power sources for powering the various components of the apparatus 10, such as through the use of batteries or power-generating elements such as piezoelectric, electromechanical, thermoelectric, and photoelectric elements. In some embodiments, portions of the user interface 28 may be included with both units 30, 32 such that each unit 30, 32 and its respective components can be individually functioned by the user.

As shown in FIG. 5, the apparatus 10 may additionally include an external systems unit 36 to enable the interface unit 30 and sensor unit 32 to easily communicate with external systems and devices. For example, the external systems unit 36 may include a communications element to communicate with the other communication elements 26, 34, a microcontroller to process information, and a standard interface such as a WiFi, Bluetooth, ANT®, USB, or ZigBee interface operable to easily interface with devices such as cellular phones, portable media players, personal digital assistants, navigation devices, personal and portable computing devices, combinations thereof, and the like. Thus, in some embodiments, the external systems unit 36 may be connected with an immobile personal computer and the interface unit 30 and sensor unit 32 may be positioned on a mobile user, as is shown in FIG. 10.

Figure 6:
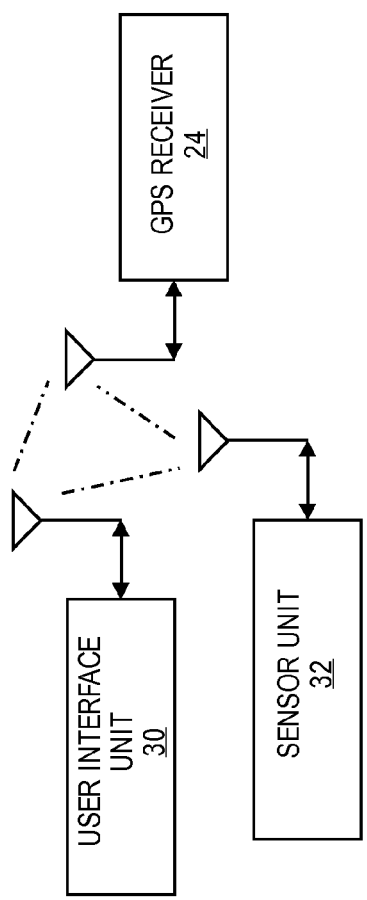
FIG. 6 is a block diagram illustrating the user interface unit and sensor unit of FIG. 5 in communication with a GPS receiver.
Figure 7:
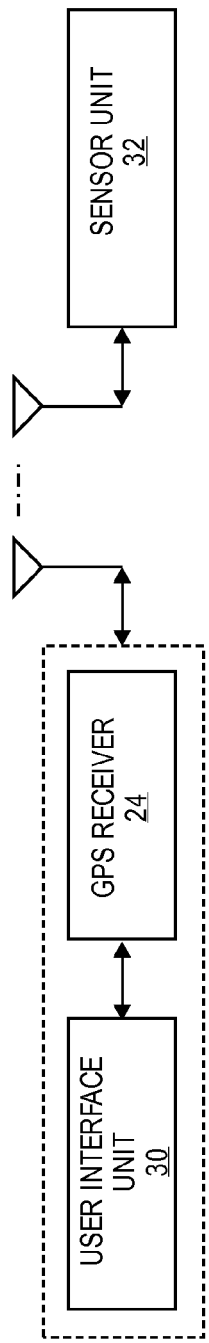
FIG. 7 is a block diagram illustrating another configuration of the user interface unit and GPS receiver of FIG. 5.

As is shown in FIGS. 6 through 9, the interface unit 30 and sensor unit 32 may each be operable to communicate with the navigation device 24 to receive and utilize navigation information. The navigation device 24 may be discrete from the units 30, 32, as shown in FIG. 6, the navigation device 24 may be integral with the interface unit 30, as shown in FIG. 7, the navigation device 24 may be integral with the sensor unit 32, as shown in FIG. 8, and/or the navigation device 24 may be integral with both units 30, 32, as shown in FIG. 9. Further, in some embodiments, any one or more of the units 30, 32, 36 and navigation device 24 may be automatically disabled when not in use to achieve optimum system power consumption and functionality.

In some embodiments, the sensor unit 32 may be attached to the user's wrist in an enclosure which is similar to a watch and combined with other functionality such as timekeeping or with other sensors such the navigation device 24. In other embodiments, the sensor unit 32 may be attached to the user's arm using an enclosure similar to an armband and combined with other devices such as a cellular phone, an audio device and/or the navigation device 24. In various other embodiments, the sensor unit 32 may be attached to the user with a chest strap in an enclosure which may include other sensors such as a heart-rate monitor (HRM). In yet other embodiments, the sensor unit 32 may be attached to user's waist with, for example, a belt clip. In further embodiments, the sensor unit 32 may be attached to the top of a user's shoe with removable fasteners such as clips. In other embodiments, the sensor unit 32 may be inserted within the user's shoe, such as within a recess formed in the sole of the shoe.

In some embodiments, the sensor unit 32, and/or more generally the apparatus 10, may be operable to attach to more than one portion of the user. For example, the sensor unit 32 may be adapted to attach to any of the various positions discussed above, including but not limited to, the user's wrist, arm, waist, chest, pocket, hat, glove, shoe (internal), and shoe (external). Such a configuration enables the same sensor unit 32, or apparatus 10, to be easily utilized by the user in a variety of positions to generate desirable motion parameters and/or to facilitate ease of use.

In some embodiments, the apparatus 10 may be configured to identify its position on the user's body, thereby allowing the user to carry or attach the apparatus 10, or more particularly the sensor unit 32, in any of the above-identified positions or in any other arbitrary location, including in combination with other electronic devices such as a cellular phone.

To identify the attachment position of the sensor unit 32, the processing system 16 may analyze one or more acceleration measurements generated by the one or more accelerometers 12. For a particular motion type such as striding, each attachment position and/or orientation will present a generally unique acceleration signature that may be identified by the processing system 16 to determine the attachment position and/or motion type of the accelerometers 12 or other portions of the apparatus 10, depending on how and/or where the accelerometers 12 are housed.

Figure 11:
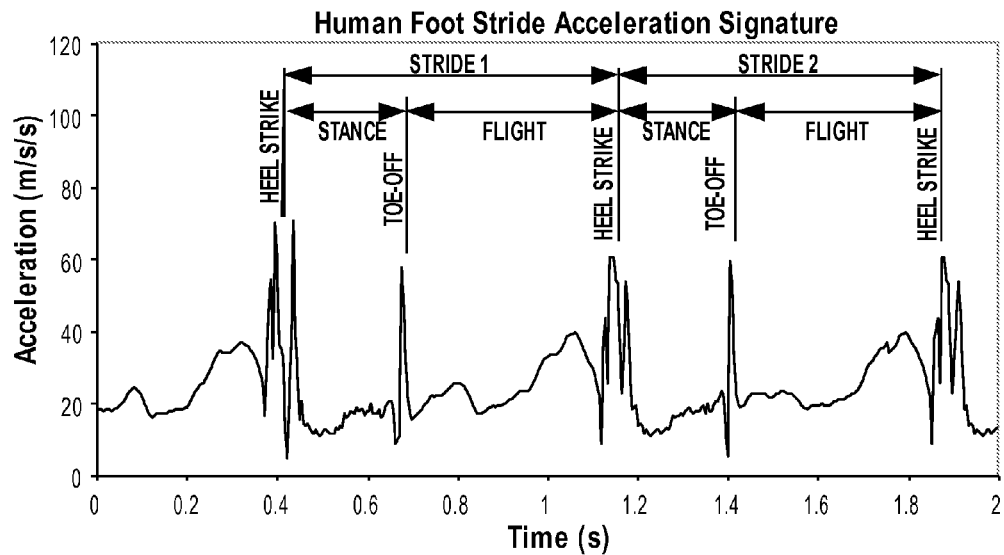
FIG. 11 is an exemplary acceleration signature for a foot-mounted sensor unit.
Figure 12:
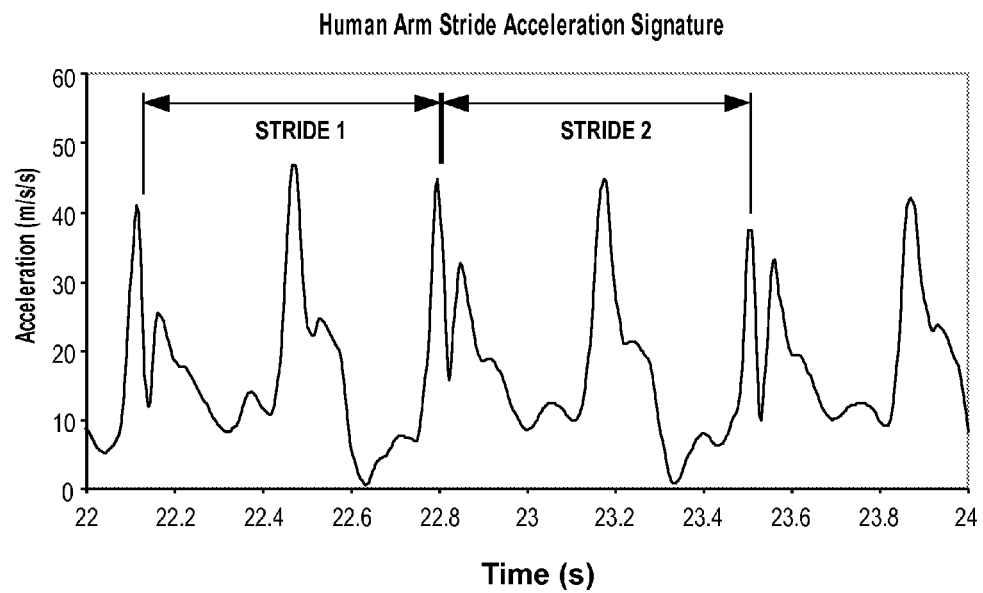
FIG. 12 is an exemplary acceleration signature for an arm-mounted sensor unit.
Figure 13:
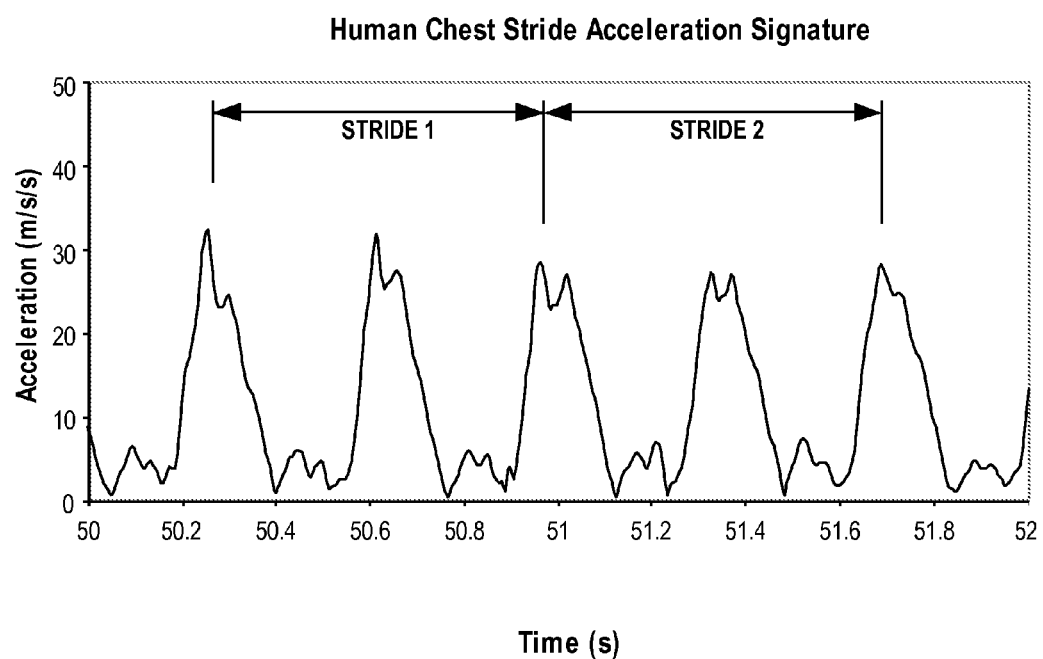
FIG. 13 is an exemplary acceleration signature for a chest-mounted sensor unit.

For example, FIG. 11 illustrates an exemplary acceleration signature corresponding to the sensor unit 32 mounted to the user's foot during striding; FIG. 12 illustrates an exemplary acceleration signature corresponding to the sensor unit 32 mounted to the user's arm during striding; and FIG. 13 illustrates an exemplary acceleration signature corresponding to the sensor unit 32 mounting to the user's chest (torso) during striding. Utilizing various signal processing algorithms, the processing system 16 may analyze measurements provided by the one or more accelerometers 12 and determine if the measurements correspond to a foot, arm, chest, or other striding acceleration signature. For example, by identifying the minimum(s), maximum(s), period, frequency, waveform, rate of change, combinations thereof, and the like, the processing system 16 may identify the acceleration signature, and thus the attachment position and/or motion type, of the sensor unit 32.

In some embodiments, the processing system 16 may determine the attachment position of the apparatus 10 by determining the orientation of the apparatus 10, or more specifically, the sensor unit 32. For example, if the sensor unit 32 is configured for mounting in two orientations, e.g., an upright orientation for mounting within a shoe and an inverted orientation for mounting on top of the shoe, the processing system 16 may analyze the acceleration measurements from the one or more accelerometers 12 to determine the orientation, e.g., upright or inverted, of the sensor unit 32 and thus where the sensor unit 32 is attached.

In some embodiments the orientation of the apparatus 10 is not associated with any particular attachment position, as described above. Instead, different orientations may be associated with different activity types, or may be indicative of other conditions such as different terrain types, use by different users, and the like. For example, if the sensor unit 32 is configured for mounting in two orientations, e.g., an upright orientation and an inverted orientation for mounting anywhere on or within the shoe, the processing system 16 may analyze the acceleration measurements from the one or more accelerometers 12 to determine the orientation, e.g., upright or inverted, of the sensor unit 32, and thus determine that the activity type is one of either jogging or bicycling.

Alternatively, for example, if the sensor unit 32 is configured for mounting in two orientations, e.g., facing forward orientation and facing backward orientation for mounting anywhere on or within the shoe, the processing system 16 may analyze the acceleration measurements from the one or more accelerometers 12 to determine the orientation, e.g., forward facing or backward facing, of the sensor unit 32, and thus determine that the user engaged in the activity is a specific one of two users.

In yet another embodiment, the sensor unit 32 is configured for mounting in one specific orientation, e.g. on a chest strap or on the belt, and the activity type, e.g. jogging or swimming, determines the orientation of the sensor unit 32 relative to gravity. The processing system 16 may then analyze the acceleration measurements from the one or more accelerometers 12 to determine the orientation, e.g., parallel or perpendicular to gravity, of the sensor unit 32, and thus determine that the activity type is one of either jogging or swimming.

The processing system 16 may identify the attachment position, orientation and/or motion type of the apparatus 10 and/or sensor unit 32 dynamically (i.e., on the fly) and/or store data corresponding to the acceleration measurements in the memory for later analysis and use. However, dynamic identification of the attachment position, orientation and/or motion type enables the processing system 16 to select an appropriate motion analysis algorithm for real-time user feedback of estimated and/or calculated motion parameters.

In some embodiments, the processing system 16 may be trained to identify new attachment positions. For example, the user could attach the sensor unit 32 in an arbitrary position, such as on the top of his or her head, and instruct the processing system 16 to enter a training mode during swimming to learn the acceleration signature of the new attachment position during the new motion type. During subsequent uses of the apparatus 10, the processing system 10 may automatically identify when the sensor unit 32 is in the new attachment position and/or when the new motion type is being performed based on the acceleration signature of the new position and/or the new motion type without requiring additional training by the user.

In some embodiments, the processing system 16 may also classify the motion currently being performed by the user based on one or more acceleration measurements provided by the one or more accelerometers 12. The processing system 16 may perform a motion classification analysis in addition to, or as an alternative to, the attachment position and motion type identification based on acceleration signature discussed above. The motion classification analysis may identify different types of gait, such as walking or running on flat or inclined surfaces, ascending stairs, descending stairs, climbing ladders, combinations thereof, and the like.

In various embodiments, the apparatus 10 includes at least two accelerometers 12 which provide signals for use by the processing system 16 to determine a striding motion angle. The two accelerometers 12 can be mounted on the foot in a substantially mutually perpendicular orientation and in the sagittal plane of the user, and generate acceleration measurements $a_0(t)$ and $a_1(t)$. A rotation sensor can be used to measure the change in angle, $\theta(t)$, in the sagittal plane. In various embodiments, the rotation sensor is a pair of spaced substantially parallel accelerometers 12 which can be used to calculate angular acceleration based on the difference of the signals. In another embodiment, the rotation sensor is a gyroscope.

Figure 14:
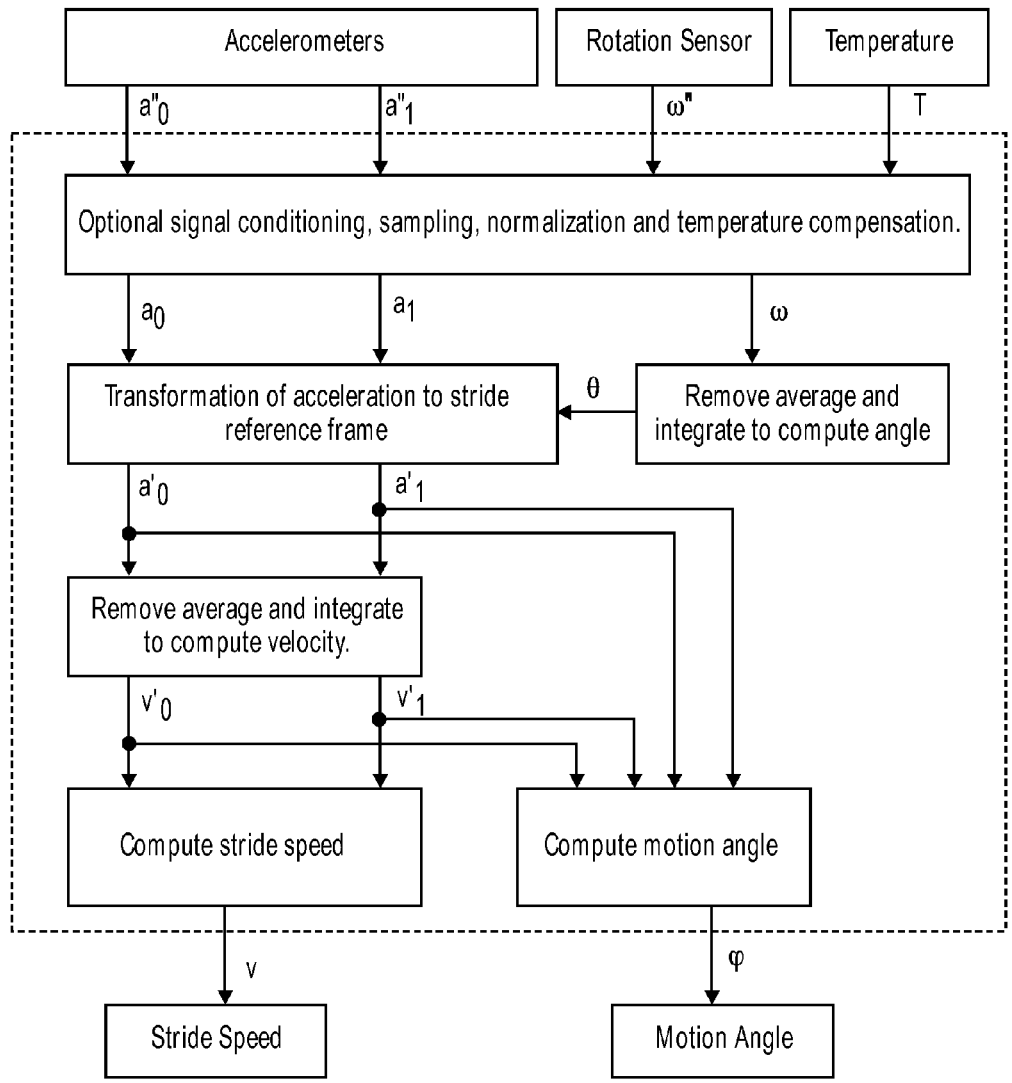
FIG. 14 is a block diagram illustrating an exemplary processing method.

Acceleration and rotational signals are sampled and stored for the duration of each stride T and processed as detailed in the exemplary block diagram of FIG. 14. The transformation of measured acceleration into the arbitrary stride reference frame within the sagittal plane can be computed by the processing system 16 as follows:

$$a_0'(t) = a_0(t)\cos(\theta(t)) - a_1(t)\sin(\theta(t)) \qquad (1)$$

$$a_1'(t) = a_0(t)\sin(\theta(t)) + a_1(t)\cos(\theta(t)) \qquad (2)$$

Mean acceleration and velocity relative to the stride reference frame can be computed by the processing system 16 as follows:

$$a_{0\,mean}' = \frac{1}{T}\int_0^T a_0'(t)dt \qquad (3)$$

$$a_{1\,mean}' = \frac{1}{T}\int_0^T a_1'(t)dt \qquad (4)$$

$$v_0'(t) = \int_0^t (a_0'(\tau) - a_{0\,mean}')d\tau \qquad (5)$$

$$v_1'(t) = \int_0^t (a_1'(\tau) - a_{1\,mean}')d\tau \qquad (6)$$

$$v'_{0\text{mean}} = \frac{1}{T}\int_0^T v'_0(t)dt \qquad (7)$$

$$v'_{1\text{mean}} = \frac{1}{T}\int_0^T v'_1(t)dt \qquad (8)$$

Stride speed can be computed by the processing system 16 as the magnitude of stride velocity as follows:

$$v = \sqrt{v'_0\text{mean}^2 + v'_1\text{mean}^2} \qquad (9)$$

The reference frame can be defined by the arbitrary orientation in the sagittal plane of the apparatus 10, or more specifically the sensor unit 32, at the start of each stride. The point of reference in time is chosen for each stride such that the sensor unit 32 is substantially stationary and the reference frame is substantially consistent between strides. Computing the average acceleration vector from the start to end of each stride yields a vector measurement that is substantially defined by gravity. This allows for the transformation of measured acceleration vector, velocity and displacement from the arbitrary reference frame to a reference frame defined by gravity.

The angle of motion can be computed by the processing system 16 from the angle of stride velocity relative to horizontal as follows:

$$\phi = \angle v - (\angle a - 90°) \qquad (10)$$

where:
φ=angle of motion relative to horizontal
∠v=angle of stride velocity relative to reference frame
∠a=angle of stride acceleration relative to reference frame $$\angle v = \tan^{-1}(v'_1\text{mean}, v'_0\text{mean}) \qquad (11)$$

$$\angle a = \tan^{-1}(a'_1\text{mean}, a'_0\text{mean}) \qquad (12)$$

The angle of motion can be calibrated for a particular subject's gait and mounting of the sensor unit 32 on the user's body. One method of calibration is to remove the average offset of motion angle from zero when the subject is walking on a flat surface.

Figure 15:
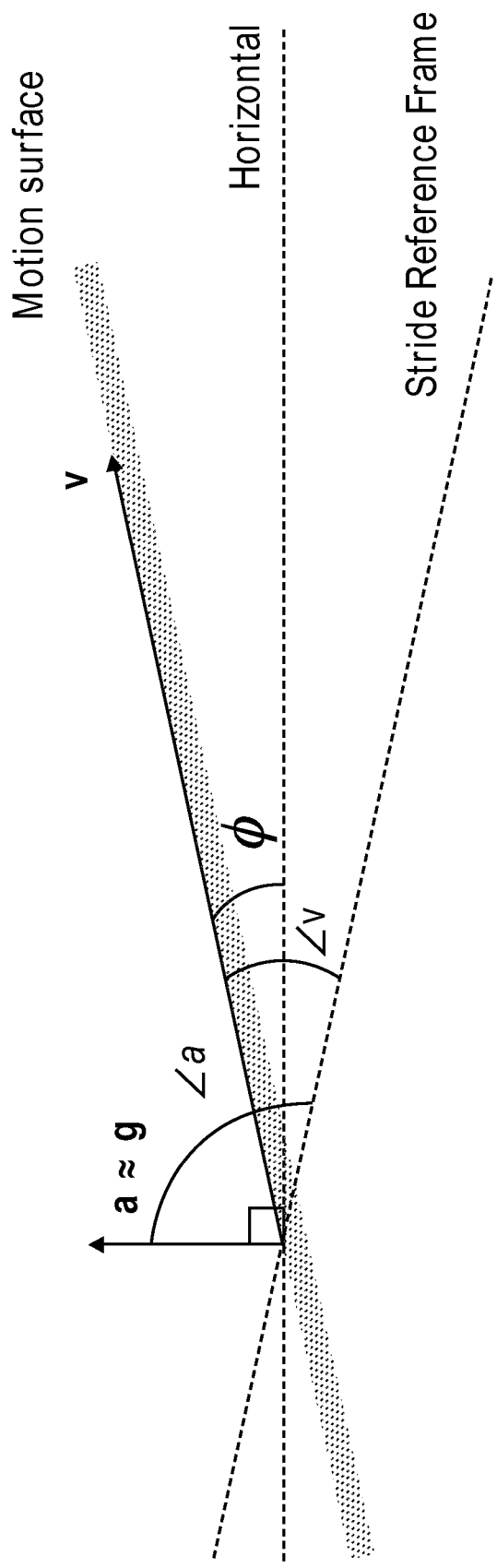
FIG. 15 is an exemplary diagram illustrating motion angle.
Figure 16:
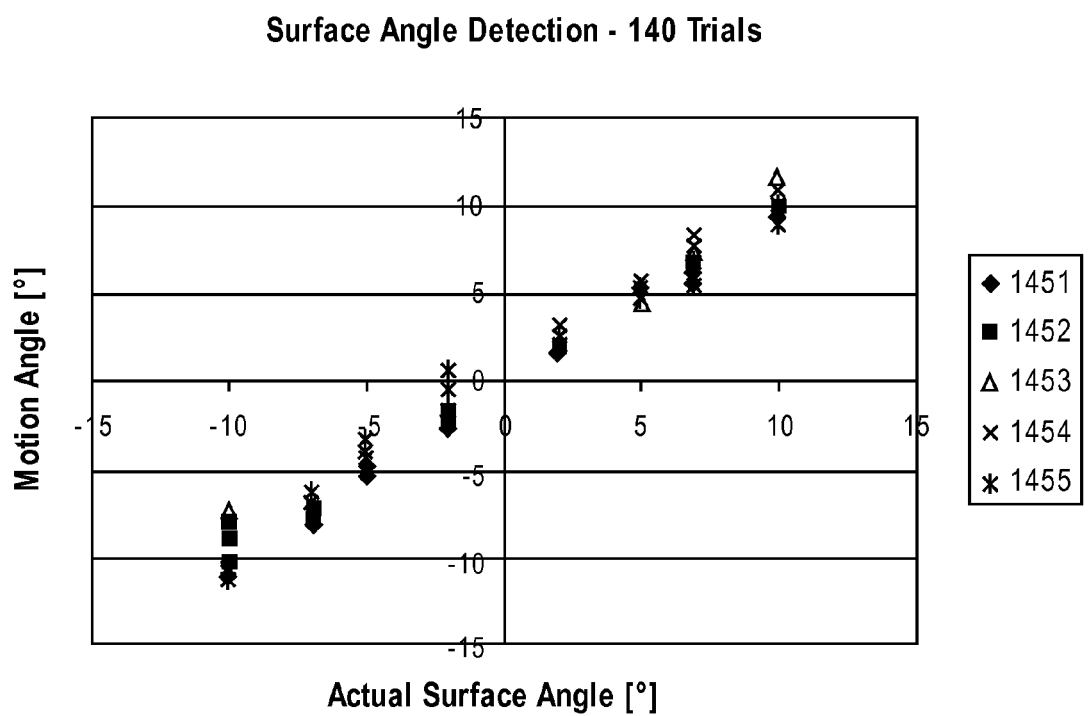
FIG. 16 is an exemplary diagram showing the relationship between motion angle and surface incline or decline.

In some embodiments, the angle of motion can be used to classify the surface incline or decline that is currently being traversed, as is illustrated in FIGS. 15-16.

In one embodiment, in addition to the two accelerometers mounted in a substantially mutually perpendicular orientation and in the sagittal plane as discussed above, a third accelerometer is included. The third accelerometer is mounted in a direction substantially perpendicular to the other two accelerometers. The acceleration measured by the third accelerometer is used to estimate the amount of motion perpendicular to the sagittal plane. This estimate may be used to compensate the motion angle measurement for motion perpendicular to the sagittal plane.

In some embodiments, the motion angle may be determined using average acceleration. Acceleration measurements provided by the one or more accelerometers 12 can be averaged to at least partially extract the DC (0 Hz) component of acceleration. Over sufficiently long time periods, DC acceleration is primarily attributable to acceleration due to gravity. Consequently, measurement of the gravity vector is used to determine the average orientation of the sensor unit 32 relative to the direction of gravity (vertical). Direction of motion can thus be estimated if the orientation of the measurement frame of reference is known relative to the direction of motion (i.e. unit mounting orientation on the body).

In one embodiment, a single accelerometer may be used. This configuration may assume that the vector representing direction of motion is in a known plane, such as the sagittal plane of the user. Under these constraints, the average acceleration measured by the accelerometer varies sinusoidally with the angle between the measurement frame of reference and vertical. The motion angle can thus be calculated by the processing system 16 if the orientation of the measurement frame of reference is known relative to the direction of motion. However, in embodiments employing the motion model discussed below, a single linear accelerometer may be employed in any orientation such that the vector representing direction of motion need not be in a known plane.

In another embodiment, two accelerometers may be used to improve accuracy over the above-described single accelerometer configuration. The two accelerometers measure accelerations in two substantially perpendicular directions, both of which are substantially within a known plane, such as the sagittal plane of the user. Combining the two acceleration measurements into an acceleration vector and averaging over sufficiently long periods of time measures the gravity acceleration vector in the measurement frame of reference. The angle of the measured gravity acceleration vector, combined with the known orientation of the measurement frame of reference relative to the direction of motion measures the motion angle.

In another embodiment, three accelerometers may be used in situations where the vector representing direction of motion is not in a known plane. The three accelerometers measure accelerations in three mutually substantially perpendicular directions. Combining the three acceleration measurements into an acceleration vector and averaging over sufficiently long periods of time measures the gravity acceleration vector in the measurement frame of reference. The angle of the measured gravity acceleration vector combined with the known orientation of the measurement frame of reference relative to the direction of motion measures the motion angle.

The motion angle determined by the processing system 16 may be used to classify the motion of the user, such as by classifying the gait of the user. An exemplary gait classification table is provided below in Table 1:

TABLE 1

| Gait Classification | Range of Motion Angle |
| --- | --- |
| Ascending Stairs | $\phi \geq 15°$ |
| Incline Walking or Running | $0° < \phi < 15°$ |
| Flat Walking or Running | $\phi = 0°$ |
| Decline Walking or Running | $-15° < \phi < 0°$ |
| Descending Stairs | $\phi \leq -15°$ |
| Backwards Walking or Running | $\phi < -165°$ or $\phi > 165°$ |

The motion angle may also be utilized by the processing system 16 to determine output power. Athletes are often interested in the amount of power output by the body during an activity. The body power output is consumed in several ways, one of which is to overcome gravity. The body power output can be calculated as the sum of the ways in which power is consumed. For a particular speed, power needed to overcome the force of gravity increases with increasing incline angle. For a particular speed, as decline angle increases the amount of power contributed to the motion by gravity increases. Gravity does not influence the output power for motion on flat surfaces. Thus, information about angle of motion may be utilized the processing system 16 to determine output power.

Acceleration measurements may also be used by the processing system 16 to classify whether or not the user's motion is cyclical. To identify cyclical motion of the sensor unit 32, the processing system 16 may analyze one or more acceleration measurements generated by the one or more accelerometers 12. One or several of many known spectral analysis techniques such as FFT, digital filtering, analogue filtering, peak counting, and the like may be employed to identify the dominant frequency components of acceleration measurements or measure the signal power in particular frequency bands. Motion could be classified as cyclical if the dominant frequency component is within a specific frequency band. Alternatively, motion could be classified as cyclical if sufficient signal power exists within a specific frequency band. For example, the specific frequency band could be 0.25 Hz to 5 Hz. Classification of the user's motion as cyclical enables the processing system 16 to calculate cadence. Cyclical components can be found in, for example, walking, jogging, running, cycling, exercising on an elliptical trainer, rowing, etc.

Acceleration measurements provided by the one or more accelerometers 12 may also be used to classify terrain type during activities such as jogging, bicycling, and the like. During activities such as jogging or bicycling, rough terrain types generate more energy in high-frequency components of acceleration measurements than smooth terrain types. To identify motion terrain type of the sensor unit 32, the processing system 16 may analyze one or more acceleration measurements generated by the one or more accelerometers 12. One or several of many known spectral analysis techniques such as FFT, digital filtering, analogue filtering, peak counting, and the like may be employed to measure the signal power in particular frequency bands. Motion terrain type could be classified as rough if sufficient signal power exists within a specific frequency band or above a specific frequency. For example, the specific frequency could be 10 Hz. Rough terrain types can be further sub-classified. For example, bicycling on shale or gravel could be differentiated from bicycling on grass or earth and rocks, based on relative signal power in specific bands above the specific frequency. Terrain classification can be used in, for example, suspension control on bicycles or in active-prosthetic control.

The processing system 16 may additionally utilize the acceleration measurements to classify striding motion. In one aspect, striding motion is classified into gait types by looking at the "stationary period". The stationary period is the amount of time the foot remains substantially stationary while walking. The stationary period can be determined by examining foot accelerations measured by the one or more accelerometers 12. The stationary period for walking is distinguishably longer than for jogging or running. Typically, the stationary period decreases as the speed of motion increases. The stationary period can be but is not necessarily equal to the duration of the stance phase.

Acceleration measurements may thus be used by the processing system 16 to classify a complete range of activities by utilizing combinations of various techniques including the acceleration signature identification, determination of angle of motion, determination of output power, identification of cyclical motion, terrain type classification, gait type classification and the like. Activities which can, for example, be classified or otherwise identified by the processing system 16 include: walking; jogging; running; swimming; bicycling; racquet sports; rowing, skiing, shuffling; driving; exercising on a stationary bicycle or other stationary apparatus such as an elliptical trainer; hiking; rollerblading; skateboarding; low-energy activities such as office activities and watching television; sleeping; dancing; playing sports such as basketball, football, soccer or golf; combinations thereof; and the like. Thus, the apparatus 10 may automatically provide information for a plurality of activities without requiring manual reconfiguration or programming by the user.

The processing system 16 may additionally or alternatively classify the user's striding motion as healthy or abnormal based on measurements provided by the one or more accelerometers 12. For example, the processing system 16 may detect irregularities in the user's gait; e.g. abnormal swing characteristics, onset of a drop-foot condition, etc, by comparing the real-time determined characteristics, such as motion angle or determined motion parameters, against known, normal, stored values. In yet another implementation, a sensor unit 32 could be worn on each foot/leg to look for gait asymmetries, for example. Such a configuration could be used in rehabilitation and training performance optimization.

In one embodiment, pronation/supination conditions are measured with a gyro, such as gyroscope housed within the sensor unit 32. The amount of foot roll in a plane substantially perpendicular to the direction of motion is measured by integrating angular velocity.

In another embodiment, pronation/supination conditions are measured with two accelerometers substantially parallel, separated by a fixed distance, such as two of the accelerometers 12 discussed above. In this aspect, the measured translational accelerations can be used to compute angular acceleration which can be doubly integrated to obtain the amount of foot roll in a plane substantially perpendicular to the direction of travel.

In another embodiment, pronation/supination conditions are measured with one of the accelerometers 12 by estimating the direction of the gravity vector relative to the orientation of the foot, before and after foot strike. This can be done with one, two or three of the accelerometers 12. One and two-accelerometer embodiments make an assumption that the accelerometer is free to rotate only in the plane substantially perpendicular to the direction of motion. A tri-axial embodiment can be mounted on the foot in an arbitrary location.

The processing system 16 may also classify motion based on the severity of impacts associated with the motion. For example, running on pavement with poor technique can be associated with substantial impacts and can thus result in substantial joint stress and wear. Exercising on an elliptical trainer, on the other hand, is associated with minimal or no impacts. Accelerometer measurements can be used to identify impact characteristics which can be used by the processing system 16 to estimate impact force and/or joint stress associated with impacts. The user may be interested in knowing instantaneous impact levels for a particular motion type, or a cumulative amount of joint stress over an activity session or over longer periods of time. Thus, the user interface 28 may inform the user of the determined motion angle, the motion classification, impact power, combinations thereof, and the like.

In one embodiment, the processing system 16 may determine the suitability of footwear for a particular user or a particular activity based on impact level measurements. In another embodiment the quality of footwear may be monitored over time with impact level measurements to determine when the footwear should be replaced.

The processing system 16 may also estimate the fatigue or efficiency of the user by identifying changes in the impact levels over time during an exercise activity as the user's foot strike will start to become more choppy and less regular, which will manifest as inconsistent acceleration patterns. Utilizing the user interface 28, the processing system 16 can also provide real-time bio-feedback as to the user's rehabilitation from a stroke or accident, for example, by denoting the level and direction of foot impact compared to established norms.

Utilizing the identified attachment position and/or the classified motion, the processing system 16 may select one or more motion analysis algorithms that may be used to determine one or more motion parameters. The memory may include a database of motion analysis algorithms corresponding to various combinations of attachment positions and motion classifications. For example, the memory may include motion analysis algorithms for: foot, chest, and arm attachment locations; walking, running, swimming, and biking algorithms; and/or walking, running, swimming, and biking algorithms for each of the foot, chest, and arm attachment positions. As should be appreciated, the processing system 16 may select a suitable motion analysis algorithm from the memory or other sources (including external sources) for any identified attachment position or classified motion. Selection of motion analysis algorithms corresponding to an identified attachment position and/or classified motion facilitates in the accurate determination of motion parameters.

The processing system 16 may additionally or alternatively select the motion analysis algorithm based on one or more user characteristics, such as age, gender, weight, height, configuration, shape, and the like. The processing system 16 may also select the motion analysis algorithm based on the configuration of the apparatus 10, such as the number and type of accelerometers 12 utilized, the number of acceleration measurements received, combinations thereof, and the like.

In some embodiments, the selected motion analysis algorithm may include a statistical model, such as a regression model selected from the group consisting of a linear regression model, a polynomial regression model, a multiple-regression model, a piecewise-linear regression model, combinations thereof, and the like.

Utilizing one or more selected motion analysis algorithms and acceleration signals provided by the one or more accelerometers 12, the processing system 16 may estimate, calculate, identify, or otherwise determine one or more motion parameters. The motion parameter may correspond to stride speed, acceleration, velocity, stride distance, total distance, gait efficiency, power, energy, maximum impact, average calories consumed, maximum speed change, speed variability, stroke power, lap time, strike time, steps, cadence, combinations thereof, and the like. However, the motion parameter determined by the processing system 16 may correspond to any parameter associated with the motion of the user.

In some embodiments, the processing system 16 may estimate the stride duration of a human or animal using measurements provided by the one or more accelerometers 12 and the selected motion analysis algorithm. For instance, based on various changes in accelerations measured by the one or more accelerometers 12, the processing system 16 may be able to determine the time at which a stride begins and ends, such as by determining when a runner's foot impacts the ground, when a runner's foot leaves the ground, when a runner's foot is stationary relative to the ground, combinations thereof, and the like. Thus, by analyzing various changes in measured accelerations, the processing system 16 may compute the stride duration and information corresponding thereto, such as stride frequency. The stride frequency may represent the number of strides per second or other indications of the rate of stride.

In some embodiments, the processing system 16 may provide the stride duration and/or stride frequency to the filtering element 14 for use in determining the various cut-off frequencies discussed above. Thus, the processing system 16 may dynamically determine the stride duration and stride frequency based on received acceleration measurements and the filtering element 14 may adapt to provide accurate filtration based on the particular performance of the user. For example, the filtering element 14 may filter perpendicular acceleration based on the stride frequency calculated by the processing system 16 to facilitate the accurate estimation of the motion parameter.

Figure 17:
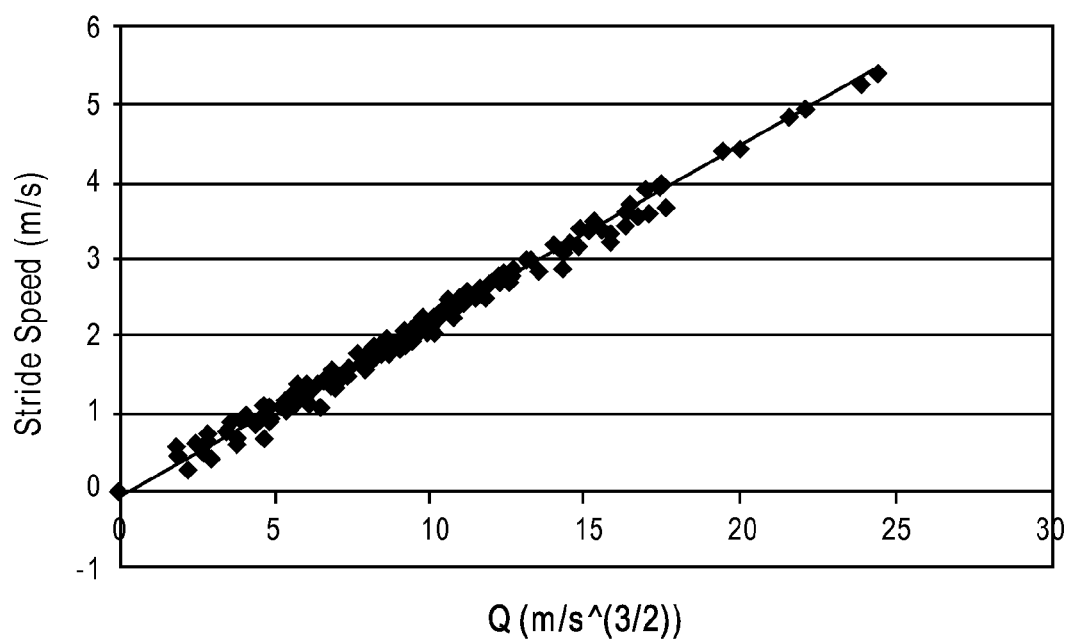
FIG. 17 is a chart showing an exemplary correlation between a motion parameter metric and stride speed.

Any motion analysis algorithm may be utilized by the processing system 16, including the motion parameter metrics and statistical models disclosed in co-pending U.S. patent application Ser. No. 11/681,032, which is incorporated by reference above. For instance, the processing system 16 may correlate a generated motion parameter metric to stride speed as shown in the regression model of FIG. 17.

The estimation/calculation/determination performed by the processing system 16 may generally correspond to any correlation between the selected motion analysis algorithm and one or more motion parameters and is not necessarily a direct computation based on user kinematics. Consequently, the processing system 16 may estimate the motion parameter utilizing statistics and/or other empirical information even when a direct computation of the motion parameter is difficult or impossible to perform.

In some embodiments, the processing system 16 may utilize a database, a look-up table, or other information stored within the memory, or any other computer-readable medium, to estimate the motion parameter using the selected motion analysis algorithm. For example, given a particular set of acceleration measurements, attachment positions, and/or classified motions, the processing system 16 may access the memory to acquire a corresponding motion parameter.

In various embodiments, the processing system 16 is operable to compute the motion parameter metric and/or estimate the motion parameter for each detected stride to facilitate the accurate analysis of movement. Thus, for every stride detected as discussed above, or for any combination of strides, the processing system 16 may estimate the motion parameter. Further, in some embodiments, the processing system 16 may estimate the motion parameter using algorithms corresponding to a plurality of strides. For example, the estimated motion parameter may correspond to a total or average stride speed resulting from several strides.

The apparatus 10 is operable to estimate motion parameters using only acceleration measurements acquired from the one or more accelerometers 12, using acceleration measurements in combination with other information acquired from the navigation device 24 or other devices through the communications element 26, using information other than acceleration measurements, combinations thereof, and the like.

In some embodiments, the processing system 16 may utilize acceleration measurements and/or other information, such as the identified attachment position or classified motion, to automatically provide appropriate content based upon the identified activity without requiring user input. For example, if the user switches from walking to jogging, the processing system 16 may identify the change, compute jogging-related metrics and motion parameters, and display jogging-related information using the user interface 28. As another example, the processing system 16 may identify that the user is swimming and that the sensor unit 32 is mounted on the user's arm based upon the acceleration measurements and generate and display swimming-related information such as cadence, stroke power, lap times, and the like.

In some embodiments, the processing system 16 may use the information received from the navigation device 24 to generate a motion parameter metric, identify the attachment position of the apparatus 10, estimate a motion parameter, and/or generate a motion model. Additionally or alternatively, the processing system 16 may use the information acquired from the navigation device 24 to correct and/or adjust calculated information. For instance, the processing system 16 may compare distances and speeds generated from accelerations provided by the one or more accelerometers 12 with distances and speeds provided by the navigation device 24 and correct calculated measurements to increase the accuracy of distances and speeds generated from measured accelerations. Thus, the processing system 16 may be periodically coupled with the navigation device 24 to correct data and information utilized by the processing system 16 to ensure that the apparatus 10 accurately estimates motion parameters even when not coupled with the navigation device 24.

Figure 20:
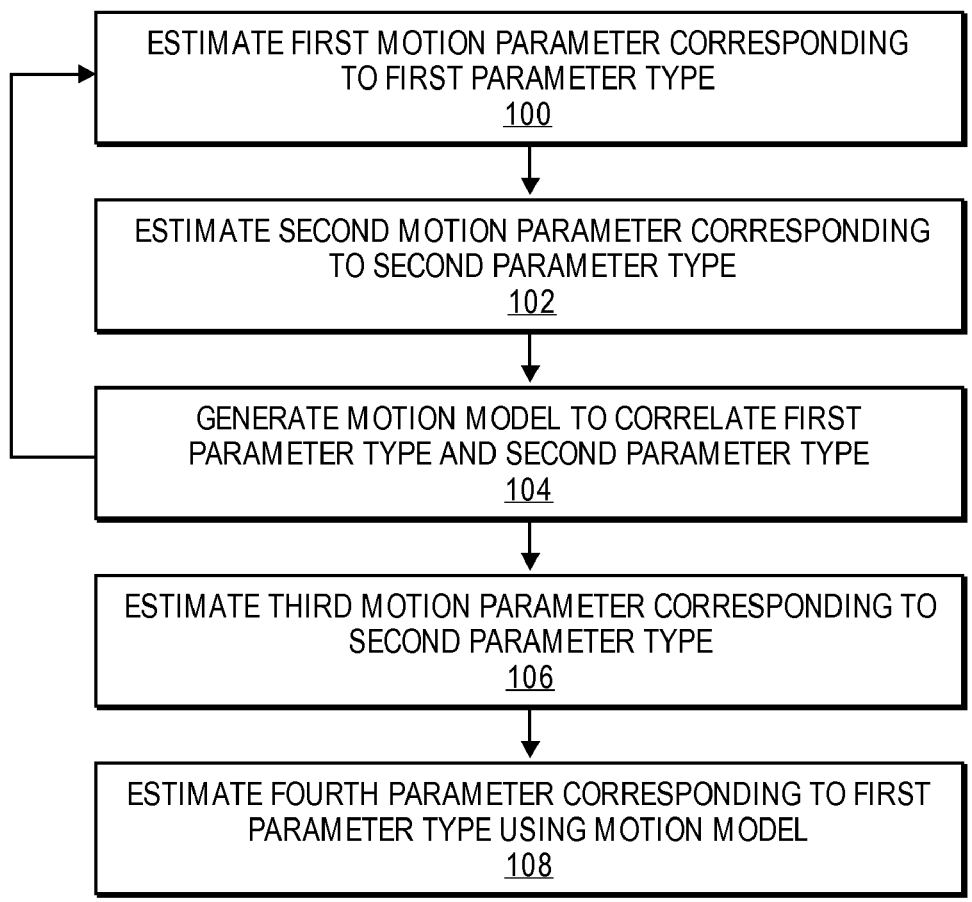
FIG. 20 is a block diagram illustrating various functions that may be performed by embodiments of the present invention.

As illustrated in FIG. 20, the processing system 16 may utilize signals provided by the navigation device 24 and the one or more accelerometers 12 to estimate motion parameters corresponding to the navigation device 24 and the one or more accelerometers 12. For example, as is illustrated in steps 100 and 102, the processing system 16 may utilize signals provided by the navigation device 24 (or signals provided by global navigation satellites) to estimate a first motion parameter corresponding to a first parameter type (e.g., user speed) and utilize signals provided by the one or more accelerometers 12 to estimate a second motion parameter corresponding to a second parameter type (e.g., user cadence). The motion parameters may be estimated in the manner discussed above using the acquired signals or by utilizing any other method. "Signal," as used herein, refers to any continuous or non-continuous communication of information through optical, electronic, and/or electromagnetic means, including a plurality of signals.

The one or more accelerometers 12, or any inertial sensor, may be coupled with the user and arbitrarily oriented relative to the direction of user motion for generation of a signal corresponding to user motion. Thus, for example, the user may place or attach the sensor unit 32, including any one or more of the accelerometers 12, in any location or combination of locations on his or her body. For instance, the user may attach the sensor unit 32 to his or her shoe, attach the sensor unit 32 to his or her arm as a watch, place the sensor unit 32 in his or her pocket or purse, combinations thereof, and the like. Thus, the one or more accelerometers 12 may generate signals to estimate the second parameter regardless of their particular orientation or attachment position. As is discussed below, embodiments of the present invention may utilize data from a single linear accelerometer in an arbitrary orientation or position due to utilization of a motion model.

As illustrated in step 104 of FIG. 20, the processing system 16 can utilize at least the first and second parameters to generate a motion model to correlate the first parameter type and second parameter type (e.g., a cadence-to-speed model). The motion model may be generated utilizing any number of parameters corresponding to the first and second parameter types, including a singular parameter corresponding to the first parameter type (e.g., the first parameter) and a singular parameter corresponding to the second parameter type (e.g., the second parameter). However, as is discussed below in more detail, the motion model may be automatically, dynamically, periodically, and/or continuously updated each time a parameter is estimated using the navigation device 24 or one or more accelerometers 12. Thus, for example, steps 100 and 102 may be periodically or continuously repeated over any time interval to update the motion model for use by the processing system 16. For example, the processing system 16 may activate the navigation device 24 for five minutes of every hour of use to retune the model and/or activate the navigation device 24 for retuning if the estimated cadence or speed is in a range where the model does not contain many data points. Further, steps 100 and 102 may be performed generally concurrently, sequentially, or in any order or progression. The generated motion model may be stored within the memory or in any other computer-readable medium.

Figure 18:
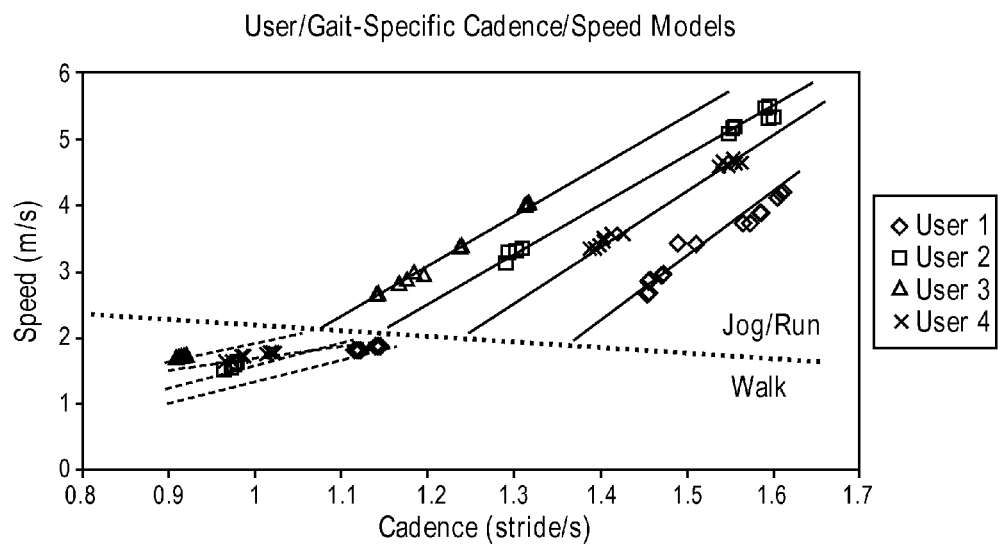
FIG. 18 is a chart showing any exemplary cadence-to-speed motion model.

Four exemplary cadence-to-speed motion models are illustrated in FIG. 18. Each of the illustrated models provides a correlation between speed and cadence. The motion model may be a mathematical function and/or plurality of mathematical functions corresponding to a relationship between the estimated parameters. For example, the processing system 16 may fit a line segment and/or curve segment to plotted parameters, such as the first and second parameters estimated and steps 100 and 102, to generate the motion model. As should be appreciated, embodiments of the present invention may employ any model-generating techniques to generate the motion model and are not limited to the exemplary techniques discussed herein.

Figure 19:
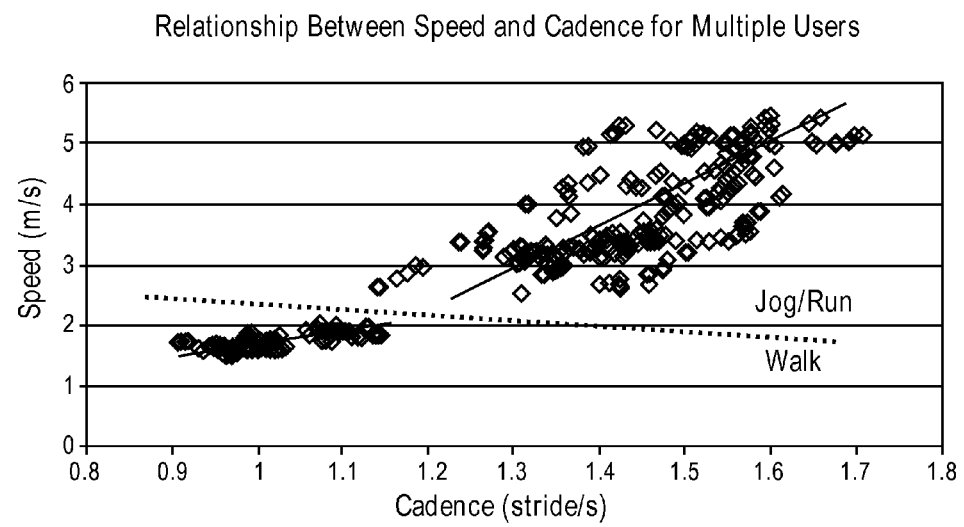
FIG. 19 is a chart showing an exemplary relationship between speed and cadence for multiple users.

Referring to FIGS. 18 and 19, the generation of the motion model utilizing parameters estimated from user movement can be desirable as it results in a user-specific model that may be used to accurately estimate future parameters for that user. For instance, as shown in FIGS. 18 and 19, the association between motion parameter types, such as speed and cadence, can vary greatly between users due to differences in how each user moves. Thus, the dynamic estimation of the motion parameters and corresponding model generation can improve the accuracy provided by embodiments of the present invention, even when a single accelerometer 12 is arbitrarily positioned on the user in any orientation to generate the second parameter.

In step 106, the processing system 16 is operable to estimate a third motion parameter corresponding to the second parameter type. In some embodiments, step 106 may be the same as step 102 such that the third motion parameter has the same value as the second motion parameter. However, in other embodiments, step 106 is performed subsequent to step 102 such that the third motion parameter and second motion parameter may have different values.

In step 108, the processing system 16 may utilize the motion model generated in step 104 and the third parameter estimated in step 106 to estimate a fourth parameter corresponding to the first parameter type (e.g., user speed). Thus, the motion model may be utilized by the processing system 16 to estimate a motion parameter represented by the model should the navigation device 24 or one or more accelerometers 12 be unavailable. For example, if the navigation device 24 is unable to receive signals to determine the location of the apparatus 10, the processing system 16 may utilize signals provided by the one or more accelerometers 12 and the motion model to estimate the motion parameter typically estimated using signals from the navigation device 24.

For instance, if the motion model is a cadence-to-speed model, signals provided by the one or more accelerometers 12 may be used to estimate a user cadence parameter and the motion model may be used to estimate a user speed parameter from the user cadence parameter. Thus, even if the navigation device 24 is not able to determine location information, or if the user decides not to employ the navigation device 24 due to time or space constraints, the motion model may still be utilized to accurately provide motion parameters to the user. The one or more parameters estimated using the motion model may be visually or audibly communicated to the user using the user interface 28.

The one or more parameters estimated using the motion model may be merged with parameters estimated using the navigation device 24 and/or one or more accelerometers 12. For example, the processing system 16 may utilize signals provided by the navigation device 24 to estimate a fifth parameter corresponding to the first parameter type (e.g., user speed) and merge the fourth parameter (e.g., also corresponding to user speed) and the fifth parameter to improve the accuracy of parameters provided by the user. For example, the processing system 16 may average or otherwise weight the fourth and fifth parameters to produce a merged parameter for use by the user.

Although user speed, user cadence, and cadence-to-speed models are discussed above, embodiments of the present invention may estimate and employ any parameters and parameter types. For example, the processing system 16 may use signals provided by the navigation device 24 to estimate user speed, user stride length, and/or variations and combinations thereof. The processing system 16 may use signals provided by the one or more accelerometers to estimate user cadence, user stride duration, and/or combinations thereof. Additionally or alternatively, the estimated motion parameters may correspond to stride speed, acceleration, velocity, stride distance, total distance, gait efficiency, power, energy, maximum impact, average calories consumed, maximum speed change, speed variability, stroke power, lap time, strike time, steps, combinations thereof, and the like. However, the motion parameters estimated by the processing system 16 may correspond to any parameter associated with the motion of the user and the motion model may represent any number of motion parameter types.

In some embodiments, the motion model may be generated utilizing devices other than the navigation device 24. For example, instead of the navigation device 24, the processing system 16 may acquire signals from the communications element 26 and/or a communications network. Thus, in embodiments where the communications element 26 includes a cellular transceiver for communicating with cellular telephone networks, the communications element 26 may receive cellular network communication signals from which the processing system 16 may estimate a motion parameter (e.g., user speed). The cellular network communication signals may themselves include a representation of the estimated motion parameter (such as a user speed derived from cellular handover signals) and/or the processing system 16 may analyze received cellular signals to estimate a motion parameter. As should be appreciated, the communications element 26 is not limited to cellular systems and any signals may be received to estimate motion parameters for use with the motion model.

In some embodiments, multiple motion models are generated and stored by the processing system 16 to accommodate multiple users. For example, a first cadence-to-speed model can be generated and stored for a first user with motion parameters corresponding to the first user and a second cadence-to-speed model can be generated and stored for a second user with motion parameters corresponding to the second user. Subsequently, the first cadence-to-speed model is used whenever the first user is using the apparatus 10 and the second cadence-to-speed model is used whenever the second user is using the apparatus 10. In some embodiments the user indicates to the apparatus 10 via user interface unit 30 whether either the first or the second user is using the apparatus 10 while in other embodiments apparatus 10 automatically determines which of first or second user is using apparatus 10 by analyzing signals from, for example, the one or more accelerometers 12.

In some embodiments, multiple motion models are generated and stored by the processing system 16 to accommodate estimation of multiple parameter types. For example, a first cadence-to-speed motion model may be generated and stored to estimate speed from cadence, and a second cadence-to-energy model may be generated and stored to estimate energy from cadence. Subsequently, either or both models may be used independently or concurrently to estimate speed and or energy from cadence.

In some embodiments, multiple motion models are generated and stored by the processing system 16 to accommodate estimation of one parameter type from multiple parameter types. For example, a first cadence-to-speed model is generated and stored to estimate speed from cadence, and a second foot-contact-to-speed model is generated and stored to estimate speed from foot contact. Subsequently, either or both models may be used independently or concurrently to estimate speed, depending on availability or perceived quality of foot-contact or cadence parameter types, or merged together.

In some embodiments, the generated motion models are communicated to external systems 36. External systems 36 may store, transfer, compare and otherwise process the generated motion models. For example, a motion model may be generated on a first apparatus 10, stored on an external system 36 and subsequently transferred back to the first apparatus 10 if the first apparatus 10 requires that the motion model be restored. Alternatively, for example, the motion model may be generated on the first apparatus 10, stored on an external system 36 and subsequently transferred to a second apparatus 10, so that the user need not regenerate the motion model on the second apparatus 10. In some embodiments, the second apparatus 10 is not itself capable of generating a desired motion model (due to, for example, lack of a navigation device) but by receiving the motion model generated on the first apparatus 10 is enabled to subsequently estimate parameters corresponding to the first parameter type. In some embodiments, an external system 36 is not necessary, and the first apparatus 10 generates and communicates the motion model to the second apparatus 10 directly.

In some embodiments, the generated motion models for multiple users are communicated to external systems 36 for analysis and comparison. For example, a cadence-to-speed model for a first user is compared to a cadence-to-speed model for a second user. The characteristics of the model itself may thus be used as a performance metric.

In some embodiments, the interface unit 30 and sensor unit 32 may be configured as a mobile phone, such as a cellular phone, including the communications element 26 for mobile communications. In such embodiments, the cellular phone may integrally include the navigation device 24 and/or be removably coupled with the navigation device 24. To generate the motion model, the user may utilize the cellular phone with the navigation device 24 enabled, and/or couple the navigation device 24 to the cellular phone. Once the motion model is generated and/or sufficiently trained, the user may disable the navigation device 24 to conserve power (or uncouple the navigation device 24 to conserve space) and utilize the generated motion model to estimate motion parameters in the absence of the navigation device 24. Thus, for example, after the motion model is trained, the user may keep the mobile phone in his or her pocket or purse and still generate useful motion parameters using the phone's internal accelerometer.

In some embodiments, the motion model may be generated utilizing signals provided by the heart rate monitor 38 worn by the user instead (or in addition to) signals provided by external sources such as the navigation device 24 or communications element 26. The signals provided by the heart rate monitor 38 may provide an indication of the user's heart rate or energy expended. In such embodiments, the processing system 16 may generate the first parameter from the heart rate monitor signals and generate the second parameter from one or more of the accelerometers 12. The first parameter, for example, may correspond to user heart rate or energy expended while the second parameter may correspond to the various parameters discussed above, including cadence. Thus, the motion model may correlate user heart rate (or expended energy) with user cadence to allow the processing system 16 to estimate parameters corresponding to user heart rate and/or expended energy even when the user is not using the heart rate monitor 38. As should be appreciated, the heart rate monitor 38 and the navigation device 24 may be utilized to generate a motion model, such as a speed-to-heart rate motion model, instead of or in addition to, the cadence-to-heart rate motion model discussed above.

In some embodiments, the motion model may be generated using signals provided only from the one or more accelerometers 12 instead of (or in addition to) signals provided by external sources. For example, the processing system 16 may estimate a first parameter (such as distance using the methods disclosed in U.S. patent application Ser. No. 11/681,032, which is incorporated above by reference) and a second parameter (such as cadence) using only signals provided by the one or more accelerometers 12. In such embodiments, the sensor unit 32 may be placed in a particular known location and orientation, such as on the user's shoe, to generate the first and second parameters and then later placed in a second location where only the second parameter (e.g., cadence) may be generated. For example, the sensor unit 32 may initially be coupled to the user's shoe and then later placed in the user's pocket (or coupled with the user's mobile phone or the navigation device 24) or in any other arbitrary location on or near the user's body. As should be appreciated, some of the accelerometers 12 may initially be coupled to the user's shoe while other accelerometers 12 may be positioned elsewhere (such as within a mobile phone positioned within the user's pocket) to enable generation of the motion model without requiring all of the accelerometers 12 to be contained within one integrated housing.

The parameters estimated by the processing system 16 may be provided to external systems, such as a database, exercise machine, computing network, combinations thereof, and the like, to improve the performance of the external systems. For example, the communications element 26 may be configured to communicate with an exercise machine, such as a treadmill, stationary bicycle, elliptical trainer, bike inclinometer, combinations thereof, and the like, to provide one or more parameters to the exercise machine for display and/or machine configuration. The exercise machine may display the fourth parameter, or any other parameter determined by the processing system 16, to the user as the parameters determined by the processing system 16 may often be more accurate than corresponding parameters determined by the exercise machine. The exercise system may also be configured to calibrate its own models and programs based on the parameters provided by the processing system 16. Further, the processing system 16 may estimate the first parameter (e.g., user speed) using signals received from the exercise machine, estimate the second parameter (e.g., user cadence) using the one or more accelerometers 12, and generate the motion model using the first and second parameters.

In some embodiments, the processing system 16 may be configured to utilize a multi-resolution approach in storing information and data corresponding to sensed measurements and activities. For example, at the lowest resolution, the time, date, classification, duration and total energy expenditure of each activity may be saved. Another resolution may allow data to be stored corresponding to, for example, for jogging, the average pace, average cadence, total distance, total elevation change, and the like. Another resolution may allow data to be stored corresponding to, again for jogging, for example, individual stride parameters and/or frequent measurements of heart rate, elevation, pace, and/or associated GPS coordinates. The history resolution depth for each type of activity can be pre-selected by the user or be automatically selected by the processing system 16 based on the amount of storage space available. In some embodiments, all activities are initially recorded at the highest available resolution; subsequently, if storage space becomes a constraint, highest resolution records of oldest activities may be erased to allow for storage of the most recent activities at a history resolution at least as good as resolution of the oldest records.

Further, the processing system 16 may provide context-aware functionality utilizing measured accelerations, identified attachment positions, classified motions, selected algorithms, estimated motion parameters, information acquired through the user interface 28, information acquired through communications element 26 or other devices such as the navigation device 24, combinations thereof, and the like. For example, the processing system 16 may detect: if the apparatus 10 is being used to estimate motion parameters or monitor user performance; if the apparatus 10 is not being used; if the apparatus 10 is being charged; if the apparatus 10 is in proximity to a compatible external system or device; if the apparatus 10 is in proximity to a display device such as a cellular phone, personal digital assistant, computer, audio device, heads-up display, watch; combinations thereof; and the like.

Based on the determination of the use context and with minimal or no user intervention, the apparatus 10 can provide any appropriate set of functions. For example, while in proximity to a compatible external system, the apparatus 10 can automatically establish a communication channel and exchange information with the compatible external system. Similarly, while monitoring user activity, the apparatus 10 can record motion history and associated motion parameters. While not in use, the apparatus 10 can disable most of its sensors to conserve energy and enable a subset of the sensors, such as the one or more accelerometers 12, only frequently enough to maintain context awareness. While in proximity to a display device, the apparatus 10 can determine the capabilities of the device, and communicate appropriate information to the display device. The use contexts are not necessarily mutually exclusive. For example, the apparatus 10 can be charging and be in proximity to a compatible external system at the same time. Thus, while charging, the apparatus 10 can continue the sensing of nearby compatible external systems and, upon detection of a compatible external system, establish a communication channel and exchange information with the compatible external system. The user thus perceives and expects the apparatus 10 to be always enabled and the apparatus 10 requires minimal or no user input to perform all of its functions.

The activity monitoring and/or context awareness discussed above may be utilized by the apparatus 10 to maintain a generally continuous record of the user's activities. For example, the user may wear the apparatus 10 continuously or repeatedly to monitor long-term activity, such as trends, goals, and the like. Generally continuous monitoring of user activity by the apparatus 10 also enables alerts to be issued if the processing system 16 detects abnormal activity. For example, if the user remains generally immobile for extended periods of time, the processing system 16 may issue an alert to notify the user through the user interface 28 and/or alert third-parties utilizing the communications element 26.

It is believed that embodiments of the present invention and many of its attendant advantages will be understood by the foregoing description, and it will be apparent that various changes may be made in the form, construction and arrangement of the components thereof without departing from the scope and spirit of the invention or without sacrificing all of its material advantages. The form herein before described being merely an explanatory embodiment thereof, it is the intention of the following claims to encompass and include such changes.

What is claimed is:

1. A system for estimating motion parameters corresponding to a user, the system comprising:
   an inertial sensor operable to couple with the user for generation of signals corresponding to user motion; and
   a processing system in communication with the inertial sensor, the processing system operable to—
      utilize a first inertial sensor signal from the inertial sensor to estimate a first user speed parameter and a first user cadence parameter,
      at least once, generate a user-specific speed-to-cadence motion model to correlate user speed to user cadence using at least the first user speed parameter and first user cadence parameter,
      utilize a second inertial sensor signal from the inertial sensor to estimate a second user cadence parameter, and
      at least once, utilize the motion model and the second user cadence parameter to estimate a second user speed parameter when the second user speed parameter cannot be directly estimated using the second inertial sensor signal.

2. The system of claim 1, wherein the inertial sensor comprises one or more accelerometers arbitrarily oriented relative to the direction of user motion.

3. The system of claim 1, further including a housing for housing the inertial sensor and the processing system.

4. The system of claim 2, wherein the inertial sensor is operable for mounting:
   in a first location to provide the first inertial sensor signal for estimation of the first user speed parameter and the first user cadence parameter; and
   in a second location to provide the second inertial sensor signal for estimation of the second user cadence parameter.

5. The system of claim 1, further including a first housing for housing the inertial sensor and a second housing for housing the processing system.

6. The system of claim 1, further including a user interface in communication with the processing system and operable to present a visual indication of the second user speed parameter.

7. The system of claim 1, wherein the inertial sensor includes a plurality of accelerometers, a first one of the accelerometers being operable for coupling with a shoe of the user and a second one of the accelerometers being integrated within a mobile phone.

8. The system of claim 1, wherein the first inertial sensor signal is the same signal as the second inertial sensor signal.

9. A method for estimating motion parameters corresponding to a user, the method comprising:
   receiving, with a processing system, a first signal from an inertial sensor to estimate a first user speed parameter and a first user cadence parameter;
   at least once, generating with the processing system a user-specific speed-to-cadence motion model to correlate user speed to user cadence using at least the first user speed parameter and first user cadence parameter;
   storing the user-specific speed-to-cadence motion model in a computer-readable memory associated with the processing system;
   receiving, with the processing system, a second signal from the inertial sensor to estimate a second user cadence parameter;
   at least once, with the processing system, utilize the motion model and the second user cadence parameter to estimate a second user speed parameter when the second user speed parameter cannot be directly estimated using the second inertial sensor signal, and
   presenting the second user speed parameter to the user.

10. The method of claim 9, wherein the inertial sensor signals are locally received from one or more accelerometers.

11. The method of claim 9, wherein the inertial sensor comprises one or more accelerometers arbitrarily oriented relative to the direction of user motion.

12. The method of claim 9, wherein the first inertial sensor signal is received from the inertial sensor mounted in a first location and the second inertial sensor signal is received from the internal sensor mounted in a second location.

13. The method of claim 9, wherein the first inertial sensor signal is the same signal as the second inertial sensor signal.

14. The method of claim 9, wherein the second user speed parameter is presented to the user using an electronic display.

* * * * *